(12) United States Patent
Kumar et al.

(10) Patent No.: US 12,702,320 B2
(45) Date of Patent: Aug. 11, 2026

(54) MRI-GUIDED ROBOTIC SYSTEMS AND METHODS FOR BIOPSY

(71) Applicant: PROMAXO, INC., Oakland, CA (US)

(72) Inventors: Dinesh Kumar, Roseville, CA (US); Aleksandar Nacev, San Francisco, CA (US); Ram Narayanan, San Jose, CA (US); Amit Vohra, Rocklin, CA (US)

(73) Assignee: Promaxo, Inc., Oakland, CA (US)

( * ) Notice: Subject to any disclaimer, the term of this patent is extended or adjusted under 35 U.S.C. 154(b) by 0 days.

(21) Appl. No.: 17/759,412

(22) PCT Filed: Jan. 22, 2021

(86) PCT No.: PCT/US2021/014628
§ 371 (c)(1),
(2) Date: Jul. 25, 2022

(87) PCT Pub. No.: WO2021/150902
PCT Pub. Date: Jul. 29, 2021

(65) Prior Publication Data

US 2023/0106912 A1 Apr. 6, 2023

Related U.S. Application Data

(60) Provisional application No. 62/965,070, filed on Jan. 23, 2020.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0036* (2018.08); *A61B 34/30* (2016.02);
(Continued)

(58) Field of Classification Search
None
See application file for complete search history.

(56) References Cited

U.S. PATENT DOCUMENTS 6,374,132 B1 * 4/2002 Acker ...................... A61N 7/02 324/309
D895,803 S 9/2020 Nacev et al.
(Continued)

FOREIGN PATENT DOCUMENTS

CN 110522491 A * 12/2019 ......... A61B 10/0233
EP 2567669 A1 3/2013
(Continued)

OTHER PUBLICATIONS

CN-110522491-A translation (Year: 2019).*
(Continued)

*Primary Examiner* — Christopher Koharski
*Assistant Examiner* — Renee C Langhals
(74) *Attorney, Agent, or Firm* — WILSON SONSINI GOODRICH & ROSATI

(57) ABSTRACT

A guided robotic system is disclosed. The guided robotic system includes a magnetic resonance imaging apparatus for real-time imaging of a subject, a computer system for analyzing images in real-time, and a robotic system for guiding a robotic arm based on real-time analysis of the images. A method of using a guided robotic system is also disclosed. The method includes acquiring live magnetic resonance images of a subject, analyzing the live magnetic resonance images to continuously identify a target portion of the subject, guiding a robotic arm towards an identified target portion of the subject based on the live magnetic resonance images, and performing a procedure at the target
(Continued)

portion of the subject. The non-limiting procedures using the guided robotic system may include, for example, biopsy, stent insertion.

19 Claims, 14 Drawing Sheets

(51) Int. Cl.
*A61B 10/04* (2006.01)
*A61B 34/20* (2016.01)
*A61B 34/30* (2016.01)

(52) U.S. Cl.
CPC . *A61B 2010/045* (2013.01); *A61B 2034/2051* (2016.02); *A61B 2034/2065* (2016.02)

(56) References Cited

U.S. PATENT DOCUMENTS

D942,012 S 1/2022 Nacev et al.
11,506,737 B2 11/2022 Gomes
D980,981 S 3/2023 Nacev et al.
11,609,291 B2 3/2023 Nacev et al.
11,656,303 B2 5/2023 Nacev et al.
11,921,178 B2 3/2024 De Matos Gomes
2011/0077504 A1* 3/2011 Fischer .................. A61B 34/30 606/130
2013/0209208 A1 8/2013 Bailey et al.
2013/0296883 A1 11/2013 Anvari
2014/0039298 A1 2/2014 Whitcomb et al.
2014/0135790 A1* 5/2014 Fenster .................. A61B 90/11 606/130
2014/0276948 A1* 9/2014 Zirps ............... A61M 25/09041 606/130
2015/0335316 A1 11/2015 Darrow et al.
2016/0213949 A1 7/2016 Uhlemann et al.
2016/0302871 A1* 10/2016 Gregerson ............. A61B 34/20
2018/0071047 A1 3/2018 Suzuki et al.
2018/0177558 A1* 6/2018 McKinley .............. A61B 34/00
2018/0356480 A1 12/2018 Weinberg et al.
2019/0069955 A1 3/2019 Popovic et al.
2020/0078097 A1* 3/2020 Gregerson ............. B25J 9/1666
2021/0338351 A1* 11/2021 Blondel ................. G16H 40/63
2022/0113361 A1 4/2022 Nacev et al.
2022/0146613 A1 5/2022 Gomes
2022/0342020 A1 10/2022 Narayanan et al.
2023/0109705 A1 4/2023 De Matos Gomes
2025/0384654 A1 12/2025 Thuy Le et al.

FOREIGN PATENT DOCUMENTS

KR 20140133209 A 11/2014
WO WO-2018081136 A2 5/2018
WO WO-2020051200 A1 * 3/2020
WO WO-2020168233 A1 8/2020
WO WO-2020172672 A1 8/2020
WO WO-2020172673 A1 8/2020
WO WO-2020198395 A1 10/2020
WO WO-2020198396 A1 10/2020
WO WO-2020264194 A1 12/2020
WO WO-2021150902 A1 7/2021

OTHER PUBLICATIONS

International Search Report and Written Opinion for International PCT Application No. PCT/US2021/014628, dated May 14, 2021.
PCT/US2021/014628 International Preliminary Report on Patentability dated Jul. 26, 2022.
AU2021209677 Office Action dated Sep. 11, 2025.
BR112022014564-0 Office Action dated Dec. 5, 2025, and a partial English translation.
CA3165780 Office Action dated Aug. 21, 2025.
CN Serial No. 2021800174779 Office Action dated Aug. 31, 2024.
EP Serial No. 21706759.4 Extended Search Report dated Feb. 6, 2025.
IL Serial No. 2893032 Office Action dated Feb. 13, 2025.
MX/a/2022/009142 Office Action dated Dec. 8, 2025, and an English translation.

* cited by examiner 400b
430
435
445

400d
455

400a
445
435
430

400c
455

MRI-GUIDED ROBOTIC SYSTEMS AND METHODS FOR BIOPSY

CROSS-REFERENCE TO RELATED APPLICATIONS

The present application is a U.S. National Stage Entry under 35 U.S.C. § 371 of International PCT Application No. PCT/US2021/014628, entitled "MRI-GUIDED ROBOTIC SYSTEMS AND METHODS FOR BIOPSY," filed Jan. 22, 2021, which claims the benefit of priority under 35 U.S.C. § 119 (e) to U.S. Provisional Patent Application Ser. No. 62/965,070, titled GUIDED ROBOTIC SYSTEM, METHODS AND APPARATUS FOR BIOPSY, filed Jan. 23, 2020, which are incorporated by reference herein in their respective entireties.

BACKGROUND

Magnetic imaging, in particular, magnetic resonance imaging (MRI) is ubiquitous in modern medicine. While MRI remains one of the best imaging modalities to perform diagnostic scans for screening, planning biopsies and planning therapy, or surgical interventions, using a MRI system for guidance during an operation or a procedure is difficult, and in some cases, with very limited success, due to a variety of issues. Some of the issues stem from, for example, the strong magnetic field needed for imaging in a MRI system. In such cases, during magnetic resonance imaging, the strong magnetic force from large magnets inside the MRI system may damage surgical or diagnostic tools that include a metallic or any magnetizable part. In some cases, the strong magnetic field may also endanger the surgeon or medical personnel in the presence of the strong magnetic field. If a robot or a robotic system is used instead of a surgeon or medical personnel for safety reasons, the strong magnetic field may still interfere with the various components of the robot, including, for example, the control system or mechanism, or interconnection joints of conjoining robotic arms, and thus possibly causing the robot to malfunction temporarily or permanently. Therefore, there is a need for a robotic system that can operate effectively and accurately in conjunction with medical imaging apparatus, such as a MRI system.

SUMMARY

In accordance with various embodiments, a guided robotic system is provided. The guided robotic system includes a magnetic imaging apparatus for continuously acquiring magnetic resonance images of a subject, a robotic arm, and a computer system for analyzing the magnetic resonance images and identifying a portion of the subject, wherein the magnetic resonance images are analyzed in real-time for guiding the robotic arm to the portion of the subject.

In accordance with various embodiments of the system, the robotic arm is attached to a component configured for drug delivery. In accordance with various embodiments, the robotic arm is configured for inserting a needle into the portion of the subject for extracting a specimen. In accordance with various embodiments, the robotic arm is configured for placing a stent into the portion of the subject. In accordance with various embodiments, the robotic arm is attached to a needle configured for removing a sample from the portion of the subject. In accordance with various embodiments, the robotic arm is configured for removing the identified portion by cutting the portion of the subject.

In accordance with various embodiments, the robotic arm is attached to an end-effector containing a plurality of needles. In accordance with various embodiments, the robotic arm is attached to an end-effector configured for carrying one or more stents. In accordance with various embodiments, the robotic arm is attached to an end-effector configured for carrying one or more brachytherapy seeds.

In accordance with various embodiments, the robotic arm is configured for extracting a specimen for examination in a medical procedure from the list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

In accordance with various embodiments, a method of using a guided robotic system is provided. The method includes acquiring live magnetic resonance images of a subject, performing image analysis of the live magnetic resonance images to continuously identify a target portion of the subject, automatically guiding a robotic arm towards an identified target portion of the subject based on the live magnetic resonance images, and performing a procedure at the target portion of the subject.

In accordance with various embodiments of the method, acquired live magnetic resonance images are displayed within a graphical user interface (GUI) that includes functional buttons for controlling the procedure. In accordance with various embodiments, acquired live magnetic resonance images comprise a high resolution image portion near a needle inserted during the procedure and a lower resolution image portion farther away from the needle.

In accordance with various embodiments, the method further includes correcting acquired live magnetic resonance images for patient motion during the performing of the procedure. In accordance with various embodiments, the method further includes correcting acquired live magnetic resonance images for motion artifacts during insertion of the needle. In accordance with various embodiments, the method further includes overriding existing action to manually correct for the patient motion. In accordance with various embodiments, the method further includes manually advancing the robotic arm by controlling the GUI using a touch input, a mouse input or a joystick input. In accordance with various embodiments, the method further includes providing a needle attached to the robotic arm, performing automatic segmentation to capture the location of the needle, withdrawing the needle, and advancing the needle to a next target location.

In accordance with various embodiments of the method, the procedure includes one from the list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

In accordance with various embodiments, a method of using a guided robotic system is provided. The method includes continuously acquiring magnetic resonance images of a subject, continuously identifying a target portion of the subject in the magnetic resonance images, guiding a needle attached to a robotic arm towards an identified target portion of the subject, wherein the magnetic resonance images are analyzed in real-time for guiding the needle to the target portion of the subject, and inserting the needle to the target portion of the subject and extracting a specimen.

In accordance with various embodiments of the method, continuously acquired live magnetic resonance images are displayed within a graphical user interface (GUI) that includes functional buttons for controlling during insertion of the needle. In accordance with various embodiments, continuously acquired live magnetic resonance images comprise a high resolution image portion near the needle and a lower resolution image portion farther away from the needle.

In accordance with various embodiments, the method further includes automatically correcting the continuously acquired live magnetic resonance images to compensate for motion blurring during insertion of the needle. In accordance with various embodiments, the method further includes automatically correcting a trajectory of the needle during the insertion based on corrected acquired live magnetic resonance images. In accordance with various embodiments, the method further includes overriding existing guided trajectory to manually correct for the motion blur. In accordance with various embodiments, the method further includes manually advancing the robotic arm by controlling the GUI using a touch input, a mouse input or a joystick input. In accordance with various embodiments, the method further includes performing automatic segmentation to capture the location of the needle, withdrawing the needle, and advancing the needle to a next target location.

In accordance with various embodiments of the method, extracted specimen is examined in a medical procedure from the list consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

In accordance with various embodiments, the guiding further includes guiding through a bore at the center of a magnetic imaging apparatus configured for continuously acquiring magnetic resonance images.

In accordance with various embodiments, a method of using a guided system is provided. The method includes acquiring live magnetic resonance images of a subject, continuously identifying a target portion of the subject in the live magnetic resonance images, guiding an end-effector attached to a mechanical arm towards an identified target portion of the subject, the end-effector carrying a plurality of needles, and inserting the plurality of needles one at a time at the target portion of the subject and extracting a plurality of specimens from the target portion of the subject.

In accordance with various embodiments of the method, acquired live magnetic resonance images are displayed within a graphical user interface (GUI) that includes functional buttons for controlling during insertion of the plurality of needles. In accordance with various embodiments, acquired live magnetic resonance images comprise a high resolution image portion near an inserted needle and a lower resolution image portion farther away from the inserted needle.

In accordance with various embodiments, the method further includes automatically correcting the acquired live magnetic resonance images to compensate for motion blurring during insertion of the plurality of needles. In accordance with various embodiments, the method further includes automatically correcting a trajectory of an inserted needle during the insertion based on corrected acquired live magnetic resonance images. In accordance with various embodiments, the method further includes overriding existing guided trajectory to manually correct for the motion blur. In accordance with various embodiments, the method further includes manually advancing the mechanical arm by controlling the GUI using a touch input, a mouse input or a joystick input. In accordance with various embodiments, the method further includes performing automatic segmentation to capture the location of an inserted needle, withdrawing the inserted needle, and inserting a further needle at a next location.

In accordance with various embodiments of the method, extracted specimens are examined in one or more medical procedures from the list consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

In accordance with various embodiments of the method, the guiding of the end-effector attached to the mechanical arm towards the identified target portion of the subject includes guiding through a bore at the center of a single-sided magnetic imaging apparatus configured for continuously acquiring magnetic resonance images.

In accordance with various embodiments, a guided robotic system is provided. The guided robotic system includes an imaging apparatus for real-time imaging of a subject, a computer system for analyzing images in real-time, and a robotic system for guiding a robotic arm based on real-time analysis of the images.

In accordance with various embodiments of the system, the robotic arm is attached to a component configured for drug delivery. In accordance with various embodiments, the robotic arm is configured for inserting a needle into the subject for extracting a specimen. In accordance with various embodiments, the robotic arm is configured for placing a stent into the subject. In accordance with various embodiments, the robotic arm is attached to a needle configured for removing a sample from the subject. In accordance with various embodiments, the robotic arm is attached to a component or a mechanism configured to provide ablation. In accordance with various embodiments, the robotic arm is attached to an end-effector containing a plurality of needles. In accordance with various embodiments, the robotic arm is attached to an end-effector configured for carrying one or more stents. In accordance with various embodiments, the robotic arm is attached to an end-effector configured for carrying one or more brachytherapy seeds.

In accordance with various embodiments of the system, the robotic arm is configured for extracting a specimen for examination in a medical procedure from the list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

In accordance with various embodiments of the system, the imaging apparatus is a single-sided magnetic resonance imaging apparatus having a bore at its center.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The novel features of the various aspects are set forth with particularity in the appended claims. The described aspects, however, both as to organization and methods of operation, may be best understood by reference to the following description, taken in conjunction with the accompanying drawings.

Figure 1A:
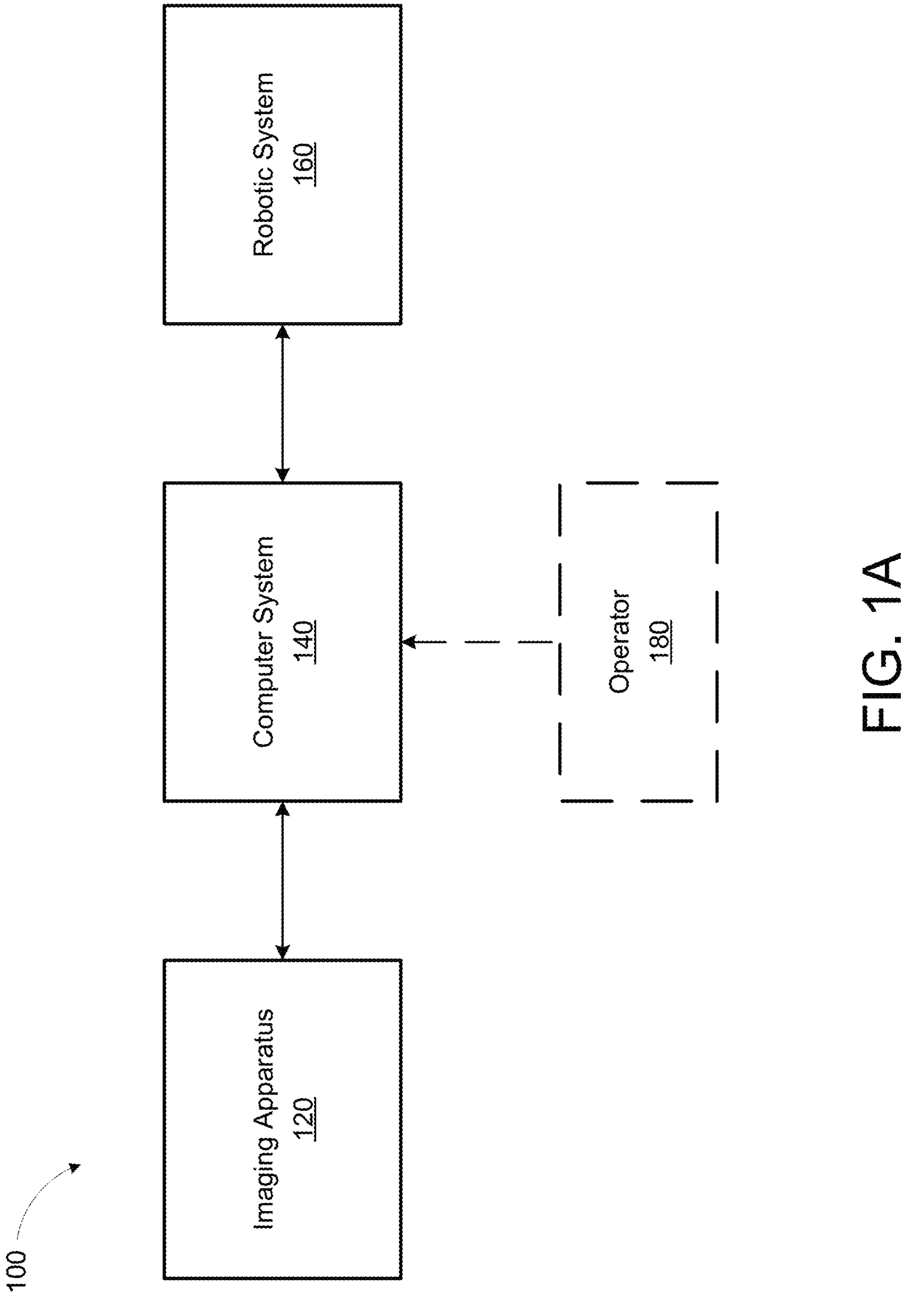
FIG. 1A is a schematic illustration of a guided robotic system, according to various aspects of the present disclosure.

The accompanying drawings are not intended to be drawn to scale. Corresponding reference characters indicate corresponding parts throughout the several views. For purposes of clarity, not every component may be labeled in every drawing. The exemplifications set out herein illustrate certain embodiments of the invention, in one form, and such exemplifications are not to be construed as limiting the scope of the invention in any manner.

DETAILED DESCRIPTION

The following international patent applications are also incorporated by reference herein in their respective entireties:

- International Application No. PCT/US2020/018352, titled SYSTEMS AND METHODS FOR ULTRALOW FIELD RELAXATION DISPERSION, filed Feb. 14, 2020, now International Publication No. WO2020/168233;
- International Application No. PCT/US2020/019530, titled SYSTEMS AND METHODS FOR PERFORMING MAGNETIC RESONANCE IMAGING, filed Feb. 24, 2020, now International Publication No. WO2020/172673;
- International Application No. PCT/US2020/019524, titled PSEUDO-BIRDCAGE COIL WITH VARIABLE TUNING AND APPLICATIONS THEREOF, filed Feb. 24, 2020, now International Publication No. WO2020/172672;
- International Application No. PCT/US2020/024776, titled SINGLE-SIDED FAST MRI GRADIENT FIELD COILS AND APPLICATIONS THEREOF, filed Mar. 25, 2020, now International Publication No. WO2020/198395;
- International Application No. PCT/US2020/024778, titled SYSTEMS AND METHODS FOR VOLUMETRIC ACQUISITION IN A SINGLE-SIDED MRI SYS- TEM, filed Mar. 25, 2020, now International Publication No. WO2020/198396; and International Application No. PCT/US2020/039667, SYSTEMS AND METHODS FOR IMAGE RECONSTRUCTIONS IN MAGNETIC RESONANCE IMAGING, filed Jun. 25, 2020, now International Publication No. WO2020/264194.

U.S. patent application Ser. No. 16/003,585, titled UNILATERAL MAGNETIC RESONANCE IMAGING SYSTEM WITH APERTURE FOR INTERVENTIONS AND METHODOLOGIES FOR OPERATING SAME, filed Jun. 8, 2018, is incorporated by reference herein in its entirety.

The following U.S. provisional patent applications are incorporated by reference herein in their respective entireties:

U.S. Provisional Patent Application No. 62/979,332, titled SYSTEMS AND METHODS FOR UTILIZING A RADIO FREQUENCY RECEIVE NETWORK FOR SINGLE-SIDED MAGNETIC RESONANCE IMAGING, filed Feb. 20, 2020;

U.S. Provisional Patent Application No. 62/987,286, titled SYSTEMS AND METHODS FOR ADAPTING DRIVEN EQUILIBRIUM FOURIER TRANSFORM FOR SINGLE-SIDED MRI, filed Mar. 9, 2020; and U.S. Provisional Patent Application No. 62/987,292, titled SYSTEMS AND METHODS FOR LIMITING K-SPACE TRUNCATION IN A SINGLE-SIDED MRI SCANNER, filed Mar. 9, 2020.

Before explaining various aspects of an MRI-guided robotic system and methods in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

In some medical procedures, such as a prostate biopsy, it is typical for the patient to endure a lengthy procedure in an uncomfortable prone position, which often includes remaining motionless in one specific body position during the entire procedure. In such long procedures, if a metallic ferromagnetic needle is used for the biopsy with guidance from an MRI system, the needle may experience attraction force from the strong magnets of the MRI system, and thus may cause it to deviate from its path during the length of the procedure. Even in the case of using a non-magnetic needle, the local field distortions can cause distortions in the magnetic resonance images, and therefore, the image quality surrounding the needle may result in a poor quality. To avoid such distortions, pneumatic robots with complex compressed air mechanisms have been designed to work in conjunction with conventional MRI systems. Even then, access to target anatomy remains challenging due to the form factor of currently available MRI systems.

The various embodiments presented herein include improved MRI systems that are configured to use for guiding in medical procedures, including, for example, robot-assisted, invasive medical procedures. The technologies, methods and apparatuses disclosed herein relate to a guided robotic system using magnetic resonance imaging as a guidance to automatically guide a robot (generally referred to herein as "a robotic system") in medical procedures. In accordance with various embodiments, the disclosed technologies combine a robotic system with magnetic resonance imaging as guidance. In accordance with various embodiments, the robotic system disclosed herein is combined with other suitable imaging techniques, for example, optical, ultrasound, x-ray, laser, or any other suitable diagnostic or imaging methodologies.

In accordance with various embodiments, the guided robotic system includes a magnetic resonance imaging apparatus for real-time imaging of a subject, a computer system for analyzing images in real-time, and a robotic system for guiding a robotic arm based on real-time analysis of the images. In accordance with various embodiments, a method of using the guided robotic system can include acquiring live magnetic resonance images of a subject, analyzing the live magnetic resonance images to continuously identify a target portion of the subject, guiding a robotic arm towards an identified target portion of the subject based on the live magnetic resonance images, and performing a procedure at the target portion of the subject. The procedure, including any invasive procedure, can include for example, but not limited to, biopsy, or stent insertion.

FIG. 1A is a schematic illustration of a guided robotic system 100, according to various embodiments. The guided robotic system 100 includes an imaging apparatus 120, a computer system 140, and a robotic system 160. In accordance with various embodiments, the guided robotic system 100 optionally includes an operator 180.

In accordance with various embodiments as described herein, the imaging apparatus 120 is a magnetic resonance imaging apparatus. In accordance with various embodiments as described herein, the imaging apparatus 120 is a single-sided magnetic resonance imaging apparatus. In accordance with various embodiments, the imaging apparatus 120 can be any imaging apparatus based on any other suitable diagnostic or imaging methodologies, including, but not limited to, for example, ultrasound, x-ray, gamma-ray, ultraviolet, infrared, visible, laser, or visual guidance based on a previously acquired scan, a mixed or augmented reality based navigation system, etc. In accordance with various embodiments, a robot is used to replace a stereotactic frame that is used for brain procedures outside of magnetic resonance imaging (MRI). In such cases, a procedure is planned using magnetic resonance scan, and the frame is registered to the magnetic resonance image and the intervention is performed using the frame with or without any image guidance.

In accordance with various embodiments as described herein, the imaging apparatus 120 is a low-field magnetic resonance imaging system that allows placement of robotic devices with adequate shielding in its vicinity. In accordance with various embodiments, the imaging apparatus 120 is configured to have a limited fringe magnetic field, and as a result, a robot or robotic arm can be placed in its vicinity without damaging the robot or the robotic arm. In accordance with various embodiments, the imaging apparatus 120 is configured to be single-sided magnetic resonance imaging system. In accordance with various embodiments, the single-sided magnetic resonance imaging system of the imaging apparatus 120 has the imaging region (e.g., a target anatomical part of the patient) that is external to the magnet assembly. In accordance with various embodiments, the magnet assembly includes a single-sided gradient coil set comprising several gradient magnetic field spiral coils configured to work in a single-sided MRI system. In accordance with various embodiments, the single-sided MRI system of the imaging apparatus 120 is configured so that the patient is covered on one side, but not completely surrounded, by the magnetic field producing materials and imaging system components. The single-sided configurations offer less restriction of patient movement while reducing unnecessary burden during situating and/or removing of the patient from the imaging apparatus 120. As such, the patient would not feel entrapped inside the imaging apparatus 120 with the placement of a single-sided gradient coil set on only one side of the patient.

In accordance with various embodiments as described herein, the imaging apparatus 120 is configured to continuously acquire images of a patient (or generally referred to herein as a "subject"). In accordance with various embodiments as described herein, the imaging apparatus 120 is configured for continuous acquisition of magnetic resonance images of the subject. In accordance with various embodiments, the imaging apparatus 120 is configured for real-time or near-real0-time imaging of the subject. In accordance with various embodiments, the imaging apparatus 120 is configured for acquiring live images, magnetic resonance images or otherwise, of the subject.

In accordance with various embodiments as described herein, the computer system 140 is coupled to the imaging apparatus 120. In accordance with various embodiments, the computer system 140 is configured for analyzing images automatically, or in real-time, and identifying a portion of the subject from the images. In accordance with various embodiments, the computer system 140 is configured for analyzing the magnetic resonance images from the imaging apparatus 120, and identifying a portion of the subject from the magnetic resonance images. In accordance with various embodiments, the computer system 140 is configured to continuously identify a target portion of the subject in the live images, magnetic resonance images or otherwise, received from the imaging apparatus 120. In accordance with various embodiments, the computer system 140 is configured to analyze images from the imaging apparatus 120 in real-time, or in near real-time, and provide guidance to the robotic system 160.

In accordance with various embodiments, the computer system 140 is configured to automatically analyze one or more images that are manually entered by a physician or an operator (and not acquired from the imaging apparatus 120), and then identify a portion of the subject from the analyzed images. In accordance with various embodiments, the computer system 140 is configured to identify a portion of the subject from one or more images that have been analyzed by a physician or an operator.

In accordance with various embodiments as described herein, the robotic system 160 is coupled to the computer system 140. In accordance with various embodiments, the robotic system 160 is configured for guiding a robotic arm (or generally referred to herein as a "robotic system") based on guidance from the computer system 140. In accordance with various embodiments, the guidance includes, for example, executable instructions, for the robotic arm. In accordance with various embodiments, the executable instructions include a set of sequential motions for the robotic arm to maneuver. In accordance with various embodiments, the executable instructions result in guiding the robotic arm towards an identified target portion of the subject. In accordance with various embodiments, the robotic arm is configured to move based on instructions from the computer system 140.

In accordance with various embodiments, the robotic system 160 includes a motion controller and a robotic arm. In accordance with various embodiments, the executable instructions from the computer system 140 are received at the motion controller for executing the instructions that result in a set of sequential motions for the robotic arm to maneuver. In accordance with various embodiments, the executable instructions result in guiding the robotic arm towards an identified target portion of the subject. In accordance with various embodiments, the robotic arm is configured to move based on instructions from the motion controller. In accordance with various embodiments, the motion controller of the robotic system 160 resides on the computer system 140.

In accordance with various embodiments, the robotic system 160 is configured for guiding a robotic arm (also referred to herein as a "mechanical arm" or "mechanical member") towards an identified target portion of the subject based on real-time analysis of the acquired images, and for guiding the mechanical arm to the portion of the subject. In accordance with various embodiments, the robotic system 160 is configured for automatically guiding a robotic arm towards the identified target portion of the subject based on analysis of the acquired images of the target portion of the subject by the imaging apparatus 120. In accordance with various embodiments, a real-time or near real-time operation of the guided robotic system 100 occurs automatically without any further input from the operator 180.

As shown in FIG. 1A, the guided robotic system 100 optionally includes the operator 180, in accordance with various embodiments. In accordance with various embodiments, the operator 180 intervenes during operation of the guided robotic system 100 where an input or intervention is needed. In accordance with various embodiments, an intervention by the operator 180 occurs, for example, during image acquisition at the imaging apparatus 120, during analysis of acquired images at the computer system 140, and/or during guidance of the robotic system 160. In accordance with various embodiments, the operation 180 intervenes when an error occurs during operation of the guided robotic system 100 or when a correction of course is needed during robotic manipulation.

Figure 1B:
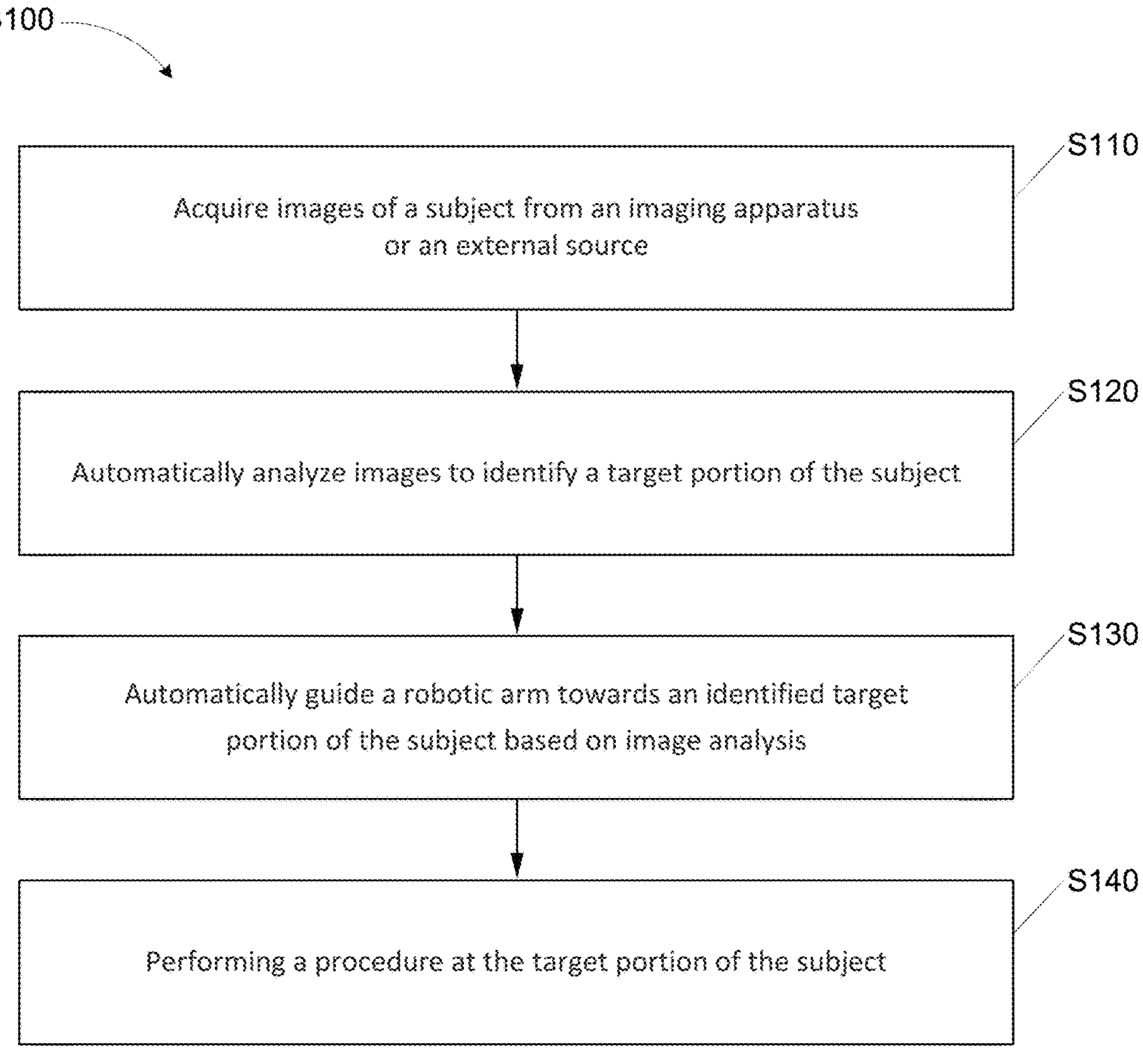
FIG. 1B is a flowchart for a method of using a guided robotic system, according to various aspects of the present disclosure.

FIG. 1B is a flowchart for a method S100 of using the guided robotic system 100, according to various embodiments. As shown in FIG. 1B, the method S100 includes at step S110 acquiring images of a subject. In accordance with various embodiments, the acquiring of the images of the subject includes acquiring one or more target anatomical parts of the subject or the patient. In accordance with various embodiments, the images are acquired from an imaging apparatus or an external source. The acquiring can be performed by any suitable imaging apparatuses or techniques based on including, but not limited to, magnetic imaging, magnetic resonance imaging, ultrasound, x-ray, gamma-ray, ultraviolet, infrared, visible, laser, or visual guidance based on a previously acquired scan, a mixed or augmented reality based navigation system, etc. In accordance with various embodiments, the images are acquired from an external source, such as a physician, a patient, a user or an operator.

As shown in FIG. 1B, the method S100 includes at step S120 automatically analyzing images to identify a target portion of the subject. In accordance with various embodiments, the acquired images are automatically uploaded into a computer system, such as the computer system 140, for analysis via one or more processes including, but not limited to, artificial intelligence (AI), machine learning, image or signal denoising, segmentation algorithms, objects and boundary identification, image registration, adaptive intensity correction, and pattern recognition, etc. In accordance with various embodiments, the acquired images are manually analyzed and entered by a physician or an operator into a computer system, such as the computer system 140, which is used to automatically identify a portion of the subject from the analyzed images.

At step S130, the method S100 includes automatically guiding (via automatic guidance) a robotic arm to an identified target portion of the subject based on the image analysis. In accordance with various embodiments, the automatic guidance includes guiding the robotic arm in real-time or near real-time based on analysis of continuously acquired images of the target portion of the subject. In accordance with various embodiments, the automatic guidance includes self-correction via image analysis. In accordance with various embodiments, the automatic guidance includes occasional interventions by a physician or an operator to correct the trajectory of the robotic arm based on acquired images. In accordance with various embodiments, the automatic guidance includes occasional interventions by a physician or an operator to alter the trajectory of the robotic arm based on acquired images in order to perform alternative or additional medical procedures.

In accordance with various embodiments of the method S100, the robotic arm is configured for movements in at least six degrees of freedom (DoF). In accordance with various embodiments, the robotic arm includes one or more mechanical arm portions that are connected in a configuration to allow the robotic arm to move, rotate, or swivel in six DoF. In accordance with various embodiments, the robotic arm is configured for accessing various anatomical parts of the subject.

In accordance with various embodiments, the robotic arm may have less than six DoF and three DoF may be sufficient for some scenarios such as transperineal biopsies where the robot only needs to move in plane (two DoF), and in and out of plan along parallel trajectories (one DoF). In accordance with various embodiments, one of two more DoF may be added to provide small rotations around x- and y-axis of the plane to allow accessing areas obscured or blocked by anatomical structures such as the pubic arch in the case of accessing the prostate.

At step S140, the method S100 includes performing a procedure at the target portion of the subject. In accordance with various embodiments, the method S100 includes performing a suitable medical procedure including for example, but not limited to, transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance, etc.

Figure 2:
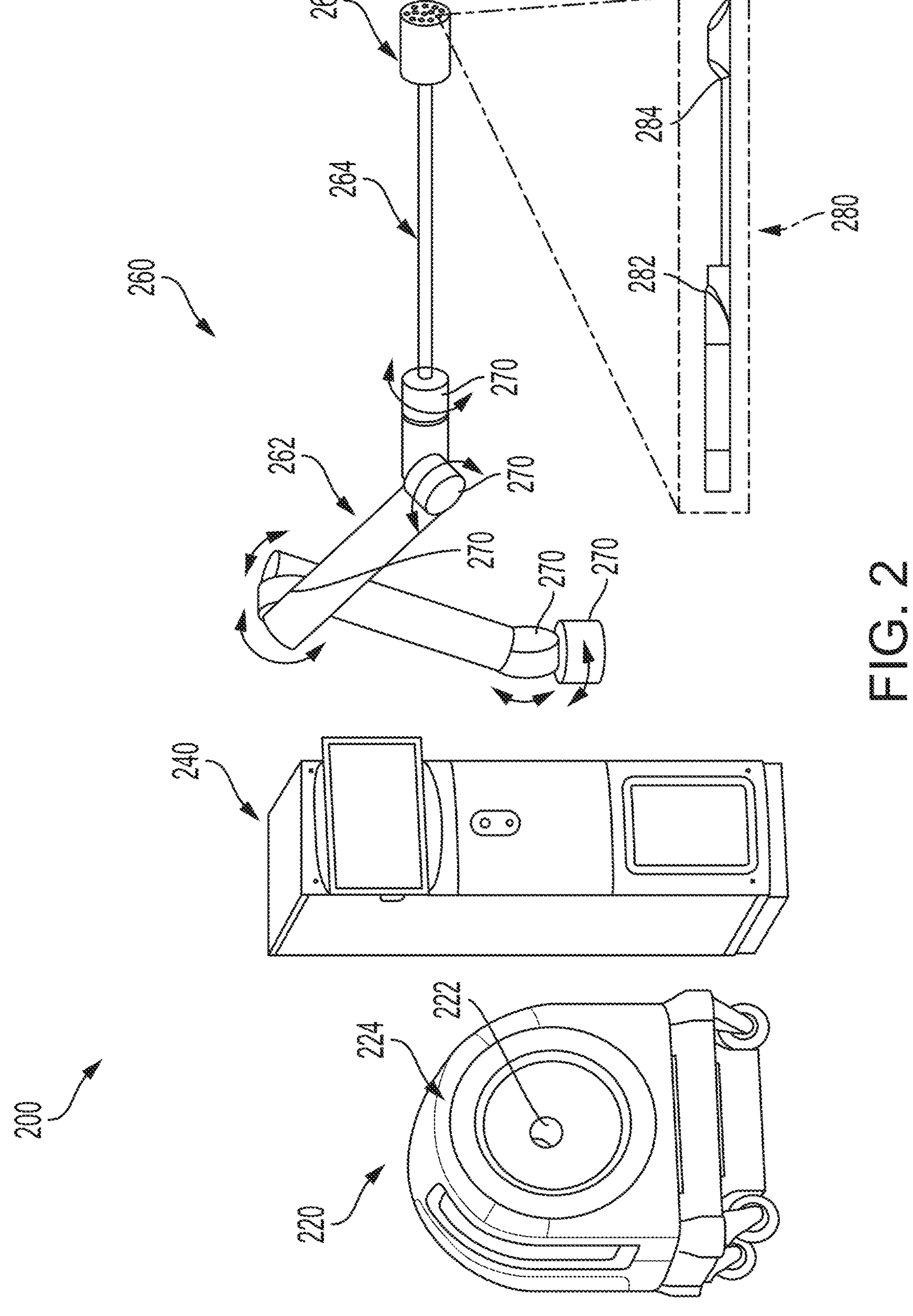
FIG. 2 is a graphical illustration another guided robotic system, according to various aspects of the present disclosure.

FIG. 2 is a graphical illustration of an example guided robotic system 200, in accordance with various embodiments. As illustrated in FIG. 2, the guided robotic system 200 includes a magnetic imaging apparatus 220, a computer system 240, and a robotic system 260. The guided robotic system 200 is similar in many aspects to the robotic system 100.

The example magnetic imaging apparatus 220 shown in FIG. 2 can include a bore 222 (also referred to herein as "access port") in the center of a single-sided magnetic coil set 224 to provide access to one or more anatomical parts of a patient being imaged during a medical procedure. In accordance with various embodiments, the magnetic imaging apparatus 220 has a fixed field of view (FOV) relative to its mechanical structure. In accordance with various embodiments, the fixed FOV is defined as a cylindrical volume with about 4 inches in diameter and about 4 inches length, or a cubic volume with sides of about 4 inches. In accordance with various embodiments, the fixed FOV ranges from about 2 inches in diameter/sides to about 12 inches in diameter/sides. In some other implementations, the FOV may be larger, such as for breast imaging applications, where a receive coil array (e.g. double receive coil) may cover a combined total of about 18-24 inches side cubes/cylinders.

Within the defined fixed FOV, the robotic system 260 can be calibrated to determine a fixed frame of reference between the robotic system 260 and the imaging FOV of the magnetic imaging apparatus 220, according to some embodiments. This calibration can ensure the robotic system 260 is operationally coupled to the magnetic imaging apparatus 220 via the computer system 240.

The setup and calibration process can include setting up the robotic system 260 and the magnetic imaging apparatus 220 for use together. In various instances, set up involves building an MR imaging phantom with at least four non-coplanar markers, which are easily identifiable in MR imaging.

To calibrate the system after set-up, the following steps can be performed. First, the phantom can be fixed rigidly in the field of view of the scanner and an image can be acquired. Second, the position of the marks can be recorded by visually identifying them on the image one at a time. This set of all points viewed on the image can be called Point Set A0 (with dimensions N×3, wherein N is the number of points identified). In certain instances, the identification can be done automatically by segmentation and/or classification. Third, the robot can be operated in free-drive mode and navigated to each Point Set A0. The position of the robot when the needle tip reaches each point in the set can be recorded. This set of all points recorded in robot coordinates can be called Point Set B0 (also with dimensions N×3). Fourth, the rigid linear least squares transformation that transforms B0 to A0 can be estimated (T: B0→A0). This is the robot-to-image transform. The inverse of this transform is the image-to-robot transform.

To test the calibration based on the transform T, the phantom can be relocated to a new position (e.g. shifted 1-2 cm in the X- and Y-directions) within the field of view. The four calibration steps above can be repeated to generate point Sets A1 and B1. Then, previously-estimated transform T can be applied to B1 to get T(B1) and the root mean squared error (RMSE) between T(B1) and A1 can be calculated. Finally, the RMSE can be verified to determine it is within an acceptable threshold and/or value.

As depicted in FIG. 2, the magnetic imaging apparatus 220 includes a single bore throughwhich a robotic arm can extend to reach a patient or target site. In other instances, the magnetic imaging apparatus 220 can include two or more access ports. Each access portion can provide access to the patient and/or surgical site. For example, in instances of multiple access ports, the multiple access ports can allow access from different directions and/or proximal locations.

Note that while FIG. 2 shows an example magnetic imaging apparatus 220 with a bore 222 in the center of a single-sided magnetic coil set, this magnetic imaging apparatus is used for exemplary purposes only. The robotic arm 262 can be configured to operate with any magnetic imaging apparatus, or imaging apparatus generally (see above discussion related to imaging apparatus 120 for examples) regardless of the apparatus design (e.g., standard MRI systems, single-sided MRI, or any other contemplated magnetic imaging apparatus or general imaging apparatus) as discussed herein.

Using a robot, instead of humans, for guiding tools for robot-assisted medical procedures can be a safer and more accurate approach in certain instances, even given some of the limitations of currently available imaging systems. These limitations can stem, for example, from the structural design and geometric architecture of, for example, current MRI systems. For example, most, if not all, current MRI systems in patient care centers utilize a magnet configuration where the patient typically lays inside a gantry (scaffold) of the MRI machine during imaging. This arrangement of magnets to surround the patient most often prohibitively limits direct access to most anatomical parts of the patient. Therefore, MRI systems (or imaging systems in general) that do not limit access to various anatomical parts of the patient can further utilize the advantages of the robot, in accordance with various embodiments, especially to be able to use it as a guidance tool in medical procedures. Such systems can therefore be additionally beneficial, particularly in robotic or robot-assisted invasive medical procedures, for targeting any anatomical parts of a patient, without constraints or limitations resulting from the confining geometry of the gantry, for example.

As shown, for example, in FIG. 2, the computer system 240 can be coupled to the magnetic imaging apparatus 220 and the robotic system 260, in accordance with various embodiments. Similar to FIG. 1, the computer system 240 can be configured for analyzing images acquired from the magnetic imaging apparatus 220 in real-time and identifying anatomical parts of the patient (or subject) from the acquired images. During operation of a medical procedure, for example, the magnetic imaging apparatus 220 is configured to acquire live (real-time) or near live (near real-time) images that may also include surgical device, such as a needle, a stent, or anything that is attached to the end of the robotic system 260, that is to be moved to the target anatomical parts of the patient for the medical procedure. Imaging the needle or the stent provides relative positioning of the needle or the stent with respect to the target portion of the anatomical parts of the patient. For example, during guidance of the robotic system 260 to insert the needle or the stent within the FOV, the plane of the acquired image containing the needle or the stent is continuously monitored rather than having to be determined manually. This provides advantages, for example, for having known the imaging plane containing the needle. In accordance with various embodiments, if the acquired images are not of sufficient quality to determine relative positioning of the needle with respect to the target portion of the anatomical parts, a higher resolution images can be acquired. In accordance with various embodiments, if the acquired images are of sufficient quality for determining relative positioning of the needle with respect to the target portion of the anatomical parts, a lower resolution images may be taken at a higher acquisition rate, which in turn provides real-time or near real-time imaging capabilities during operation of the medical procedure. In accordance with various embodiments, the image acquisition rate of the magnetic imaging apparatus 220 ranges from about 3-10 images per second to about one image per five minutes depending upon the resolution. In accordance with various embodiments, the image acquisition rate of the magnetic imaging apparatus 220 ranges is up to about 60 or 120 images per second.

In accordance with various embodiments, the robotic system 260 is configured to be placed outside the magnetic imaging apparatus 220. As shown in FIG. 2, the robotic system 260 can include a robotic arm 262 that is configured for movements in 6-degrees of freedom. In accordance with various embodiments, the robotic arm 262 includes one or more mechanical arm portions (also referred to herein as one or more components), including a hollow shaft 264 and an end-effector 266, that are connected in a configuration to allow the robotic arm 262 to move, rotate, or swivel in 6-degrees of freedom via one or more motion controllers 270. The double-headed curved arrows signify rotational motions produced by the motion controllers 270. In accordance with various embodiments, one or more motion controllers 270 is an actuator, such as a mechanical actuator, including but not limited to servomotors. In accordance with various embodiments, one or more motion controllers 270 is an actuator, such as a pneumatic, spring-loaded, mechanical, electrical motor, piezoelectric actuator, or combinations thereof.

In accordance with various embodiments, the robotic arm 262 of the robotic system 260 is configured for accessing various anatomical parts of interest through or around the magnetic imaging apparatus 220. In accordance with various embodiments, the bore 222 in the center of the magnetic imaging apparatus 220 is specifically designed to provide access to the robotic arm 262 of the robotic system 260 for operation at various anatomical parts of interest of the patient during a medical procedure. In accordance with various embodiments, the bore 222 in the center of the magnetic imaging apparatus 220 is designed to account for the size of the robotic arm 262. For example, the bore 222 defines a circumference that is configured to accommodate a robotic arm therethrough, such as the various robotic arms described herein. In accordance with various embodiments, the robotic arm 262 of the robotic system 260 is configured for accessing various anatomical parts of the patient from around a side of the magnetic imaging apparatus 220. Magnetic imaging apparatuses are further described in U.S. patent application Ser. No. 16/003,585, titled UNILATERAL MAGNETIC RESONANCE IMAGING SYSTEM WITH APERTURE FOR INTERVENTIONS AND METHODOLOGIES FOR OPERATING SAME, filed Jun. 8, 2018, which is incorporated by reference herein in its entirety.

In accordance with various embodiments, the hollow shaft 264 provides the housing for the mechanism to actuate the end effector and may contain a long screw drive, shaft or another mechanism to provide the quick end effector action necessary to take the biopsy samples. Additionally, the hollow shaft may be able to store multiple needles and/or sampled cores.

In accordance with various embodiments, the end-effector 266 is attached to one end of the robotic arm 262, as illustrated in FIG. 2. In accordance with various embodiments, the end-effector 266 includes a mechanism, an actuator, a housing or configuration to store or carry one or more needles 280, and/or insert the one or more needles 280, or a housing or configuration to store, carry and/or insert one or more stents or brachytherapy seeds. In accordance with various embodiments, the end-effector 266 includes a mechanism to insert the needles 280 to obtain a biopsy sample, a component or a mechanism to provide ablation, or a component or a mechanism to perform brachytherapy, among many other suitable medical procedures (also referred to herein as interventions). In accordance with various embodiments, the needles 280 are used for extracting a specimen, wherein the specimen can be attached to a needle 280, drawn into a needle 280, or via any other mechanism for which the specimen can be extracted using a needle 280. In accordance with various embodiments, the end-effector 266 has a minimal mechanical or pneumatic control to select the needle 280 to be inserted. In accordance with various embodiments, the motion or movement of the robotic arm 262 inserts or withdraws the needle 280.

In accordance with various embodiments, the one or more mechanical arm portions of the robotic arm 262, including the hollow shaft 264 and the end-effector 266, are made of non-magnetic materials and do not include any electrical components, such as for example, servomotors for motion control. In such a configuration, all the degrees of motion, such as servomotors, for the robotic system 260 can remain outside the bore 222 on one side of the magnetic imaging apparatus 220 facing away from the patient. This configuration allows safe storage of the robotic system 260 away from the magnets of the magnetic imaging apparatus 220. With this configuration, in accordance with various embodiments, the robotic system 260 can extend using the one or more mechanical arm portions of the robotic arm 262 to reach across to the target portions of the patient through the bore 222. In accordance with various embodiments, the robotic system 260 can extend using the one or more mechanical arm portions of the robotic arm 262 to reach the target portions of the patient around the magnetic imaging apparatus 220, instead of through the bore 222. The configuration for reaching around is suitable for extremities or breast biopsies, where a needle (attached to the end-effector of the robotic arm 262) can be inserted from the side of the patient in an orthogonal direction. In accordance with various embodiments, the needle is inserted in an imaging plane and the needle trajectory is calibrated to lie in the imaging plane.

In accordance with various embodiments, the needles 280 include any non-magnetic material, such as titanium, non-magnetic stainless steel, ceramics, etc. In certain instances, the needles 280 can be entirely non-magnetic to reduce interference with the magnetic imaging apparatus.

In accordance with various embodiments, image distortion can occur locally when a magnetic stainless steel needle is used, which is a common practice in certain instances. If there is distortion due to using a magnetic needle or other magnetic surgical device, then the distortion can be removed with image processing. A benefit of using a non-magnetic needle is that it would not cause distortion to the image. In accordance with various embodiments, the needle 280, such as a biopsy needle, includes an outer cylindrical sleeve 282 and an inner core 284, as shown in FIG. 2. The inner sleeve has a recessed region for containing the sampled tissue. For example, during a medical procedure or intervention, the inner sleeve cuts through the tissue first, with tissue setting into the recess. In such cases, the outer sleeve follows shortly and cuts the tissue so that a sample of tissue remains in the recess.

In accordance with various embodiments, a hollow needle is used to place a stent or brachytherapy seeds. In accordance with various embodiments, the hollow needle includes an outer sleeve and an inner needle that pushes out the stent/seeds at the appropriate locations.

In accordance with various embodiments, the needles 280 include gauge sizes ranging from 12 G to 18 G, including 10 G, 12 G, 14 G, 16 G, and 18 G. In accordance with various embodiments, the needles 280 are sized 16 G to 18 G for biopsy, and 10 G for brachytherapy or ablation. In accordance with various embodiments, the needles 280 have a range of lengths for prostate procedures between about 15 cm and 25 cm.

In accordance with various embodiments, the magnetic imaging apparatus 220 is a low-field magnetic imaging system with a fixed geometry. During operation of such low-field magnetic imaging system, sufficiently low-field magnet may not interfere with the shielded robotic servo-motors. However, the presence and operation of these components may interfere with the magnetic field produced by the magnetic imaging apparatus 220 during operation. To eliminate or reduce potential interference during magnetic imaging, the robotic system 260 is configured with the robotic arm 262 that can be extended via the one or more mechanical arm portions, including the hollow shaft 264 and the end-effector 266 through the bore 222 of the magnetic imaging apparatus 220. In such instances, the entire robotic tool can be distal to the bore 220 and outside the magnetic imaging apparatus 220 during a surgical procedure. In accordance with various embodiments, the magnetic imaging apparatus is designed to have a cylindrical region that is aligned with the bore 222 and has lower magnetic interference than other regions within the imaging zone. For example, the robotic tool can be positioned far enough from the coils and in the region of the imaging zone with the weakest magnetic field, gradient field, and/or RF field. Such a cylindrical region can be where the robotic arm 262 extends into and operates in various aspects. To further reduce or avoid potential magnetic interferences from the robotic system 260, all or most of the components of the robotic arm 262 can be constructed from non-magnetic material. In accordance with various embodiments, the magnetic imaging apparatus 220 is kept close to the patient and away from sources of magnetic interference. For example, the motors for the robotic arm and/or robotic tool can be positioned outside of the bore 222. In such instances, referring to FIG. 14, the patient is proximate to the magnetic imaging apparatus 220, and the magnetic imaging apparatus is between the patient and the robotic system. A distal portion of the robotic arm can reach through the magnetic imaging apparatus 220 to reach the patient. In accordance with various embodiments, active noise cancellation techniques can be used to sense the noise generated from the motors and then remove it from the acquired MRI signals. In accordance with various embodiments, signal processing can be used to remove any noise generated from the motors. For example, to remove the noise generated by the motors, the MRI signal can be combined with a motor noise removal signal that is actively generated to produce a noiseless MRI signal. Low-field magnetic imaging systems are further described in International Application No. PCT/US2020/018352, titled SYSTEMS AND METHODS FOR ULTRALOW FIELD RELAXATION DISPERSION, filed Feb. 14, 2020, now International Publication No. WO2020/172673, 168233, which is herein incorporated by reference in its entirety.

Figure 3A:
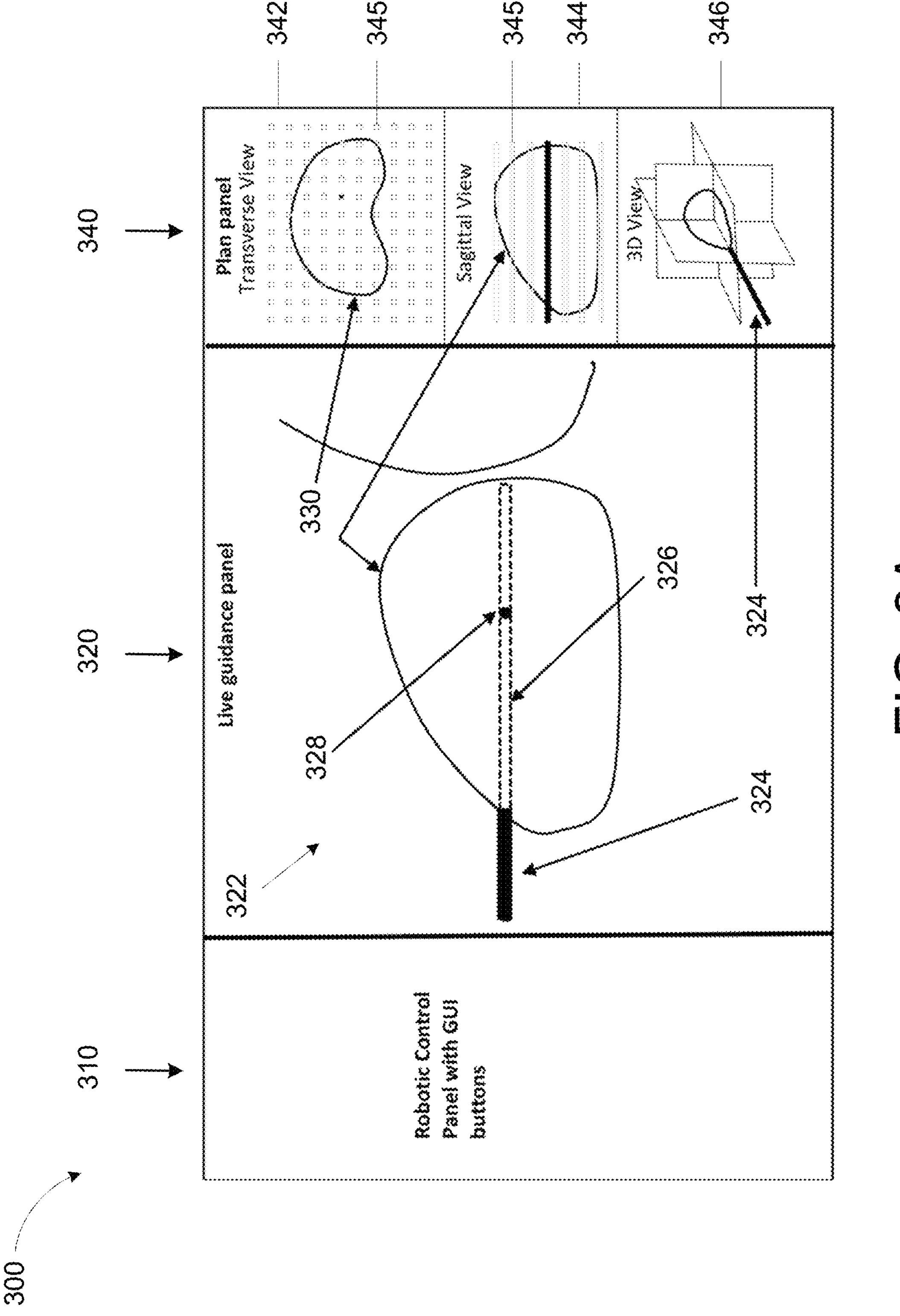
FIG. 3A is a schematic illustration of a graphical user interface of a guided robotic system, according to various aspects of the present disclosure.

FIG. 3A is a schematic illustration of a graphical user interface (GUI) 300 for an example guided robotic system, according to various embodiments. As shown in FIG. 3A, the GUI 300 includes a left panel 310, a middle panel 320, and a right panel 340. The GUI 300 shown in FIG. 3A is for illustrative purposes, and thus is a non-limiting example user interface. As a non-limiting example, the GUI 300 is configured for use in the invasive operating procedure, a robotic transperineal prostate biopsy.

As illustrated in FIG. 3A, the left panel 310 shows a plurality of buttons for robotic control. In accordance with various embodiments, the buttons are operated or activated by capacitive touching, a mouse input, or joystick input by an operator. In accordance with various embodiments, the left panel 310 includes touch-screen controls for controlling the robot and for various imaging adjustments. In accordance with various embodiments, the left panel 310 includes controls for overriding previous inputs, including certain user actions, for example, but not limited to, changing previous trajectory of the needle movement. In accordance with various embodiments, the left panel 310 may include a button for motion correction during live scans of the subject.

The middle panel 320 includes a live guidance view showing live images 320 (the term "live" also refers to herein as "continuously captured" or "continuously acquired") of a portion of a target 330 (e.g., prostate 330), a current needle position 324, a current needle trajectory 326, and a target sample location 328 within the prostate 330. During a surgical procedure and/or intervention, "live" images are obtained intraoperatively. In accordance with various embodiments, the middle panel 320 shows live scanned images being acquired, which include the current needle position 324, the needle trajectory 326, and the target 330 automatically identified from the scan. As the needle advances into the field of view shown on the live guidance view in the middle panel 320, the lives images 320 continuously display the current location of the needle, i.e. updated current needle position 324. In the background (e.g., processing behind the scene), this view is continuously registered with the corresponding view from a pre-procedure image to compensate for the motion, according to some implementations. For example, every time there is a scan, a new image is produced and re-registered with the corresponding view from a pre-procedure image to compensate for any movement.

As shown in FIG. 3A, the right panel 340 includes various views of the planning scan, including for example, a transverse view 342, a sagittal view 344, and a three-dimensional (3D) view 346. The transverse view 342 shows a slice from the planning scan containing the target 330. In accordance with various embodiments, a virtual grid 345 is used to show evenly spaced potential needle locations, which are shown in the transverse view 342 as hollow circles. The sagittal view 344 shows the sagittal image containing the target 330. In accordance with various embodiments, the virtual grid 345 is used to show evenly spaced potential needle locations, which are shown in the sagittal view 344 as horizontal lines. According to some embodiments, the lines represent the potential needle trajectories due to the transperineal approach along the transverse direction. The 3D view 346 displays a cross-sectional view from the planning image based on the current needle location 324 and updates the graphic on the GUI (e.g. GUI 300) as the needle is advanced distally.

Figure 3B:
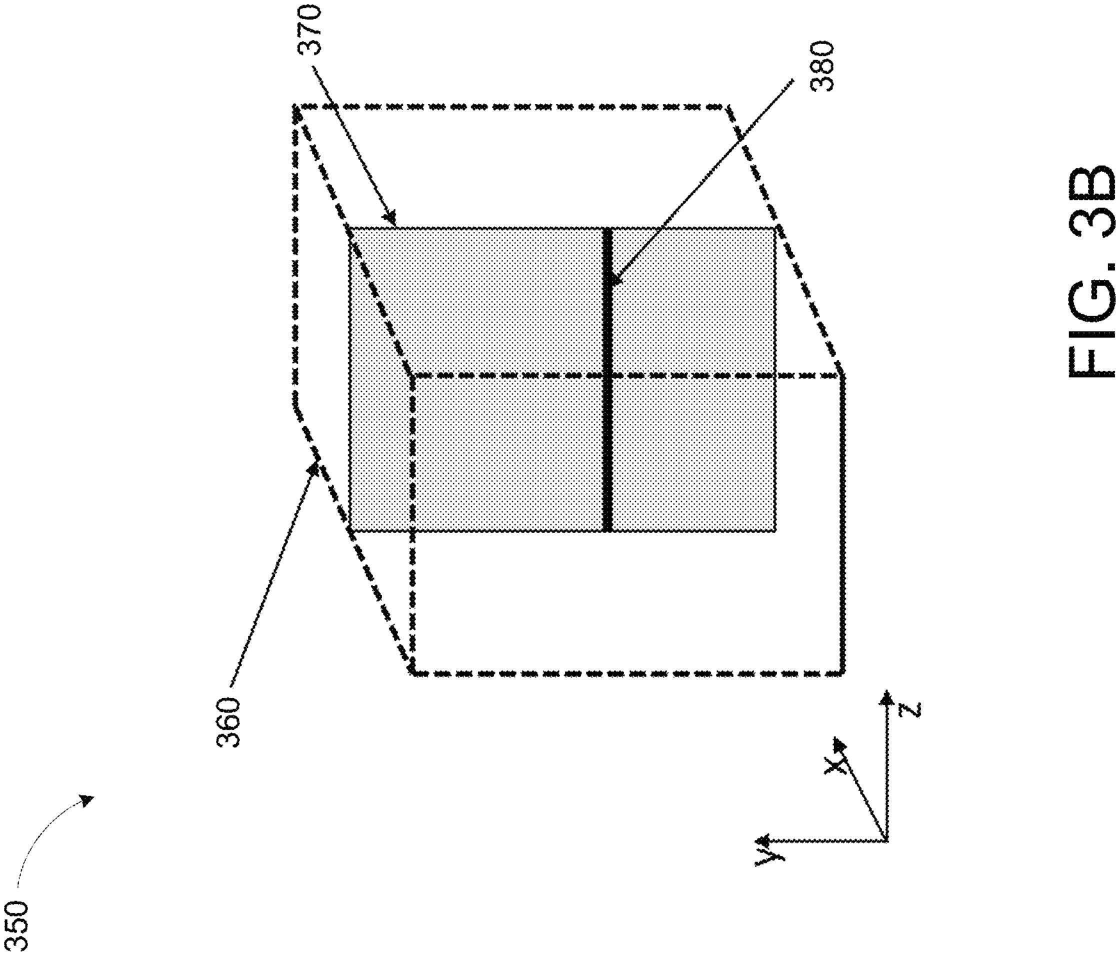
FIG. 3B is a schematic illustration of a live view during imaging of a guided robotic system, according to various aspects of the present disclosure.

FIG. 3B is a schematic illustration of a live view 350 during imaging of a guided robotic system, according to various embodiments. As illustrated in FIG. 3B, the live view 350 is in the x-y-z coordinate system, designated by a dotted cube along the x, y, and z axes. The imaging needs to be acquired only in the plane in which the needle is expected, which is represented by imaging plane 370 in the middle of the field of view 360 in the FIG. 3B. In accordance with various embodiments, the live view 350 has a built-in z-gradient and can excite one or more slabs of varying thickness within the field of view 360. An alternative embodiment, may not have the z axis gradient built-in. In accordance with various embodiments, the x- and y-gradients are embedded as phase-encodes for the imaging in the imaging plane 370 containing the needle. The spatial localization of points within the field of view 360 are determined by a combination of x and y phase encodes, and transmit frequency band corresponding to the z-gradient. These slabs are different from the conventional image slices and through image reconstruction, and therefore, can be broken into a number of slices.

In accordance with various embodiments, slice interleaving is utilized in which the system can excite the entire field of view by multiplexing excitation of different slabs within the field of view 360 to completely cover the entire field of view 360 by transmitting and receiving different bandwidths at different time intervals within the pulse sequence. Based on only y-phase encodes (due to the z-phase being built in the system) can produce a two-dimensional cross-sectional image containing the needle at a fast speed. For example, utilizing slice interleaving in a single dimension (e.g. the needle trajectory) can be done at a high resolution and fast rate. In accordance with various embodiments, there is virtually no acquisition and computing cost associated with obtaining a thick slab, while using only y-phase encodes using slice interleaving approach, where the sampling is done only in one dimension.

As illustrated in FIG. 3B, the live view 350 is configured to show a projected needle trajectory 380 within the imaging plane 370. According to some implementations, the needle is advancing in the positive z-direction in the x-y-z coordinate system as illustrated in FIG. 3B. In accordance with various embodiments, the whole volume is imaged at a lower detail and then the region around the needle trajectory 380 is imaged in finer detail during live guidance to show accurate positioning of the needle. In accordance with various embodiments, a hybrid image that contains a higher resolution portion of the image closer to the needle and a lower resolution image portion elsewhere in the image may be sufficient. The hybrid imaging approach can offer further improvements in imaging acquisition time, i.e., faster imaging, while maintaining sufficient details in the area that is needed to determine accurate positioning of the needle with respect to the position of the target 330.

Additional trade-offs between image acquisition rates versus resolution of the acquired images may be achieved by suitable optimization techniques using hardware and/or software approaches, such as compressed sensing using k-space under-sampling, parallel imaging, and multi-slice image acquisition. These techniques aim to speed up image acquisition with the typical cost of image signal to noise ratio. They leverage data symmetries and data compression techniques to acquire the minimal amount of data necessary to reconstruct the image.

Some target anatomies such as the prostate present unique challenges for needle guided interventions. The prostate, for example, is surrounded by soft tissue and is prone to movement as a result of any pressures from transrectal transducers or needle entering into the prostate. For example, as the needle is inserted into the prostate, the prostate may be pushed away and upon insertion, the gland may settle back into its original or into some other location. Similarly, when withdrawing the needle, the gland may continue to push back and change its location. This becomes particularly problematic when one is trying to use a rigid frame of reference with the robot as the registration between the anatomy and the imaging may become erroneous.

In accordance with various embodiments, a motion correction method is used to dynamically estimate the motion using image similarity metrics between the live image and the corresponding cross-section from the planning image. In accordance with various embodiments, this is further enhanced by motion detection and correction in the k-space itself. Correction in k-space ensures that the reconstructed image does not have motion artifacts, whereas the image-based registration minimizes the error caused by motion in accurate placement of the robot. For example, gross patient motion and localized gland deformations can be separated by using magnetic resonance visible fiducial markers and corrected for separately. Motion can be determined from comparing frames of MRI images, for example. The measured motion is applied to the robot frame of reference, which is known by the robot, and the target anatomy and the robot maintain their correspondence. For example, the measured motion is applied to update the target anatomy and the robot frame of reference to allow the robot to move in the correct path relative to the target anatomy. Fiduciary markers can also be used to determine correspondence.

For guided robotic procedure or intervention, magnetic imaging scans are taken for the target anatomy for planning the procedure. These scans (planning scan) may include magnetic (e.g., magnetic resonance) image scans using one or more contrast types. The images may manually or automatically be classified into suspected malignancies for biopsies and into the malignancy extents for an image-guided therapy. In accordance with various embodiments, the image guided procedure may be performed immediately after the planning images are acquired, i.e., live imaging, or at a later time. In accordance with various embodiments for the procedure to be performed at a later time, a pre-procedure anatomical scan is performed to map the planning image into the current frame of reference. The following figures illustrate various embodiments of the procedures that utilize guided robotic procedure.

FIGS. 4A, 4B, 4C, 4D, 5A, 5B, 5C, 5D show different views (e.g. transverse and sagittal views) for a virtual template-based or grid-based approach.

Figures 4A, 4B, 4C, 4D:
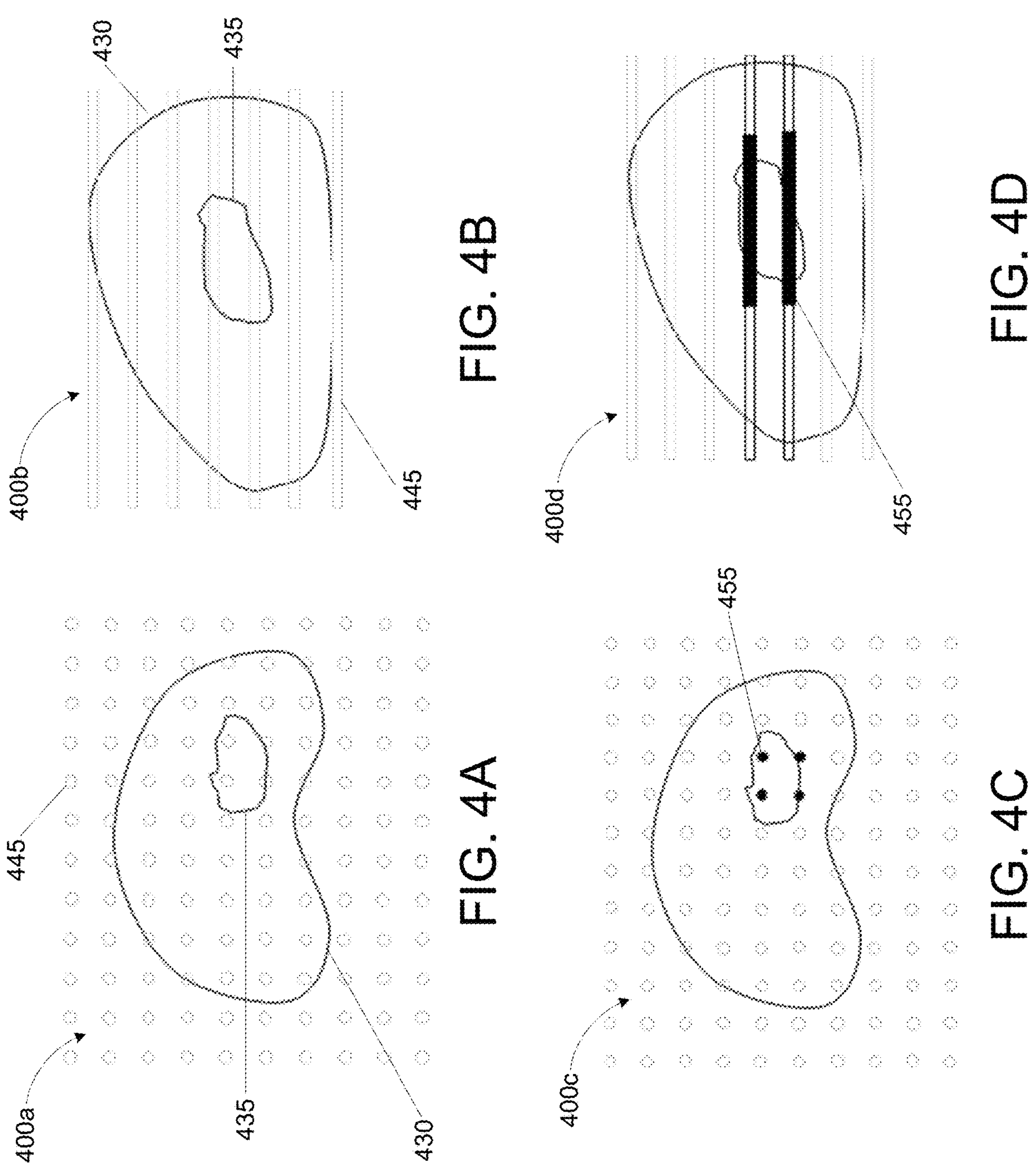
FIG. 4A is a schematic illustration showing a transverse image during a planning scan of a prostate sample, according to various aspects of the present disclosure.
FIG. 4B is a schematic illustration showing a sagittal image during a planning scan of a prostate sample, according to various aspects of the present disclosure.
FIG. 4C is a schematic illustration showing a transverse image for a biopsy plan based on the planning scan illustrated in FIG. 4A, according to various aspects of the present disclosure.
FIG. 4D is a schematic illustration showing a sagittal image for a biopsy plan based on the planning scan illustrated in FIG. 4B, according to various aspects of the present disclosure.

FIG. 4A is a schematic illustration showing a transverse view 400*a* during a planning scan of a prostate sample 430, according to various embodiments. FIG. 4B is a schematic illustration showing a sagittal view 400*b* of the prostate sample 430, in accordance with various embodiments. As illustrated in FIGS. 4A and 4B, the planning image of the prostate sample 430 can be marked to show a suspected region 435 (e.g., possibly malignant or confirmed malignant) in both transverse view 400*a* and sagittal view 400*b*. Also shown in FIGS. 4A and 4B is a virtual template grid 445, which is illustrated as evenly spaced hollow dots for potential needle locations in FIG. 4A and straight lines for potential needle trajectories in FIG. 4B. In accordance with various embodiments, the spacing of the hollow dots can vary based on desired needle locations or trajectories.

FIG. 4C is a schematic illustration showing a transverse view 400*c* for a biopsy plan based on the planning scan illustrated in FIG. 4A, according to various embodiments. FIG. 4D is a schematic illustration showing a sagittal view 400*d* for the biopsy plan based on the planning scan of the prostate sample 430 illustrated in FIG. 4B. As illustrated in FIG. 4C, four locations (e.g. four filled dots) of the grid 445 where a biopsy sample can be obtained from the suspected region 435 are shown at sample locations 455. Similarly, FIG. 4D shows two straight trajectory lines of the grid 445 in the sagittal view 400*d* that correspond to the sample locations 455, which encompass the suspected region 435. The biopsy plan, illustrated by filled circles and straight lines cover the entire target suspected region 435.

Figures 5A, 5B, 5C, 5D:
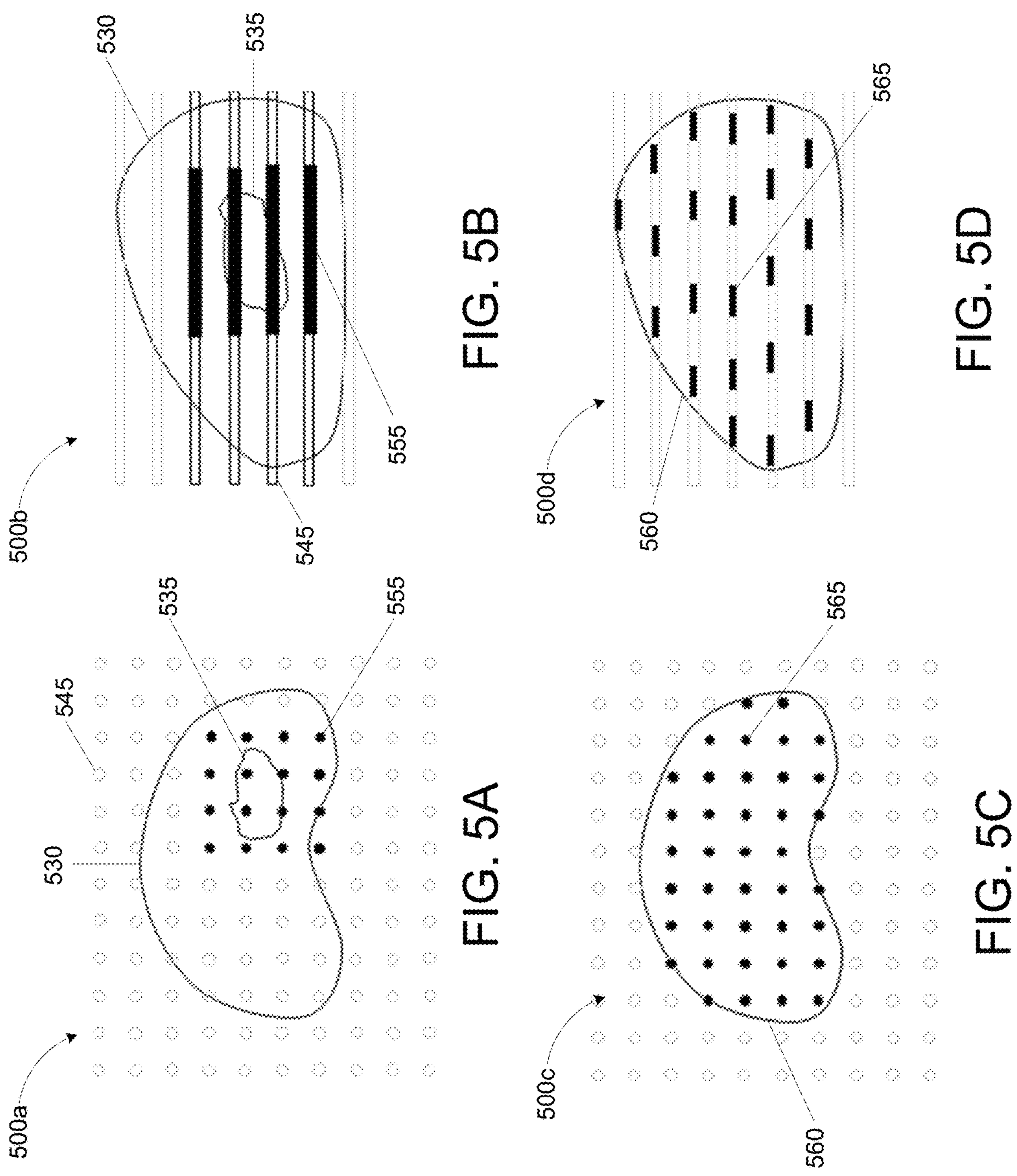
FIG. 5A is a schematic illustration showing a transverse image for a biopsy plan that provides an extent of malignancy of a prostate sample, according to various aspects of the present disclosure.
FIG. 5B is a schematic illustration showing a sagittal image for a biopsy plan that provides an extent of malignancy of a prostate sample, according to various aspects of the present disclosure.
FIG. 5C is a schematic illustration showing a transverse image for a low-dose brachytherapy plan of a prostate sample, according to various aspects of the present disclosure.
FIG. 5D is a schematic illustration showing a sagittal image for a low-dose brachytherapy plan of a prostate sample, according to various aspects of the present disclosure.

FIGS. 5A and 5B respectively illustrate a transverse view 500*a* and a sagittal view 500*b* of a prognosis plan to determine extents of the malignancies by placing a bounding box of a prostate sample 530, according to various embodiments. As illustrated in FIGS. 5A and 5B, the prognosis plan for the prostate sample 530 is marked to show a suspected region 535 (e.g., possibly malignant or confirmed malignant) in both transverse view 500*a* and sagittal view 500*b*. Also shown in FIGS. 5A and 5B is a virtual template grid 545, which is illustrated as evenly spaced hollow dots for potential needle locations in FIG. 5A and straight lines for potential needle trajectories in FIG. 5B. The prognosis plan of the prostate sample 530 as illustrated in FIGS. 5A and 5B provides the bounding box, illustrated by sample locations 555, which are shown as sixteen filled dots in FIG. 5A and four filled lines in FIG. 5B. The sample locations 555 encompass a suspected or known malignancy in the suspected region 535 to determine the extent of the prognosis. This prognosis may be used for determining the disease management pathway, such as active surveillance, or type and extent of the procedure.

FIG. 5C is a schematic illustration showing a transverse view 500*c* for a low-dose brachytherapy plan of a prostate sample 560, according to various embodiments. FIG. 5D shows a schematic illustration of a sagittal view 500*d*, in accordance with various embodiments. The low-dose brachytherapy plan for the prostate sample 560 shown in FIGS. 5C and 5D is illustrated by sample locations 565, which are shown as filled dots within the entire prostate sample 560 in FIG. 5C and dashed lines within the entire prostate sample 560 in FIG. 5D. In accordance with various embodiments, the low-dose brachytherapy may be used to treat the prostate sample 560 as illustrated in FIGS. 5C and 5D. In some other embodiments, the low-dose brachytherapy may be used to treat a portion of the prostate sample 560.

Figures 6A, 6B:
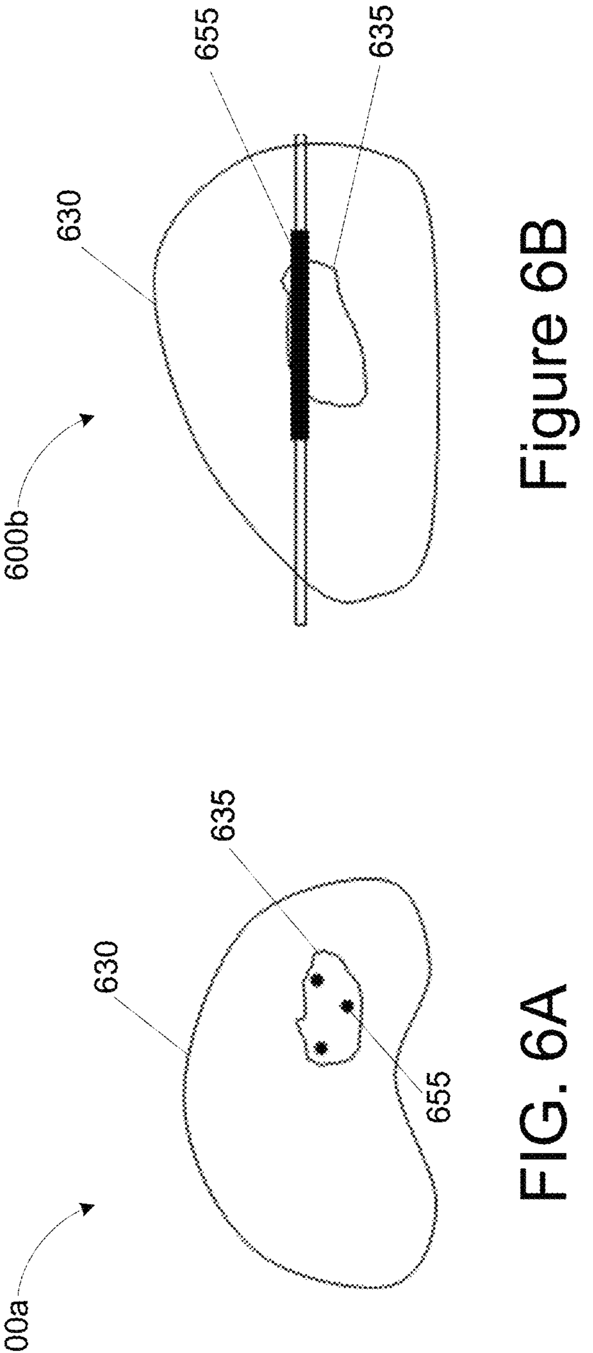
FIG. 6A is a schematic illustration showing a transverse image without a virtual grid for a biopsy plan of a prostate sample, according to various aspects of the present disclosure.
FIG. 6B is a schematic illustration showing a sagittal image without a virtual grid for a biopsy plan of a prostate sample, according to various aspects of the present disclosure.

FIG. 6A is a schematic illustration showing a transverse view 600*a* for a biopsy plan of a prostate sample 630 without a virtual grid, according to various embodiments. FIG. 6B shows a schematic illustration of a sagittal view 600*b* for the biopsy plan of the prostate sample 630, in accordance with various embodiments. As illustrated in FIGS. 6A and 6B, the biopsy plan for the prostate sample 630 is marked to show a suspected region 635 (e.g., possibly malignant or confirmed malignant) in both transverse view 600*a* and sagittal view 600*b*. As illustrated, the biopsy plan for the prostate sample 630 shown in FIGS. 6A and 6B are not restricted by the grid for needle insertion. The biopsy plan of the prostate sample 630 as illustrated in FIGS. 6A and 6B includes some selected sample locations 655 in the suspected region 635. The sample locations 655 are shown as 3 filled dots in FIG. 6A and a filled line in FIG. 6B.

In accordance with various embodiments at described herein, the robotic system 260 of FIG. 2 can be used for any of the procedures or interventions illustrated and described with respect to FIGS. 4A, 4B, 4C, 4D, 5A, 5B, 5C, 5D, 6A, and 6D. As shown in FIG. 2, the robotic system 260 includes the robotic arm 262 configured for movements in 6-degrees of freedom. After calibration at an origin within the imaging field of view shown, for example, in FIG. 3A or 3B, the robotic arm 262 can move the needle tip to any point in the x-y plane, for example, as shown in FIG. 3B. In accordance with various embodiments, the robotic arm 262 can align to any point in the grid pattern of the overlaid virtual template, for example, as shown in FIG. 4A, 4C, 5A or 5C, or any other location within the field of view in a template-free approach, for example, as shown in FIG. 6A. In accordance with various embodiments, the needle insertion is performed by advancing the robotic arm 262 along the z-direction, as shown in FIG. 3B, or from left to right or vice versa as shown in FIG. 4B, 4D, 5B, 5D, or 6B.

As the described above, in accordance with various embodiments, the robotic arm 262 is configured to include one or more motion controllers 270, such as an actuator, or the end-effector 266 at the end of the arm that can hold one or more short needles. In accordance with various embodiments, the actuator 270 is completely mechanical and is triggered by a servo motor near the base of the robotic system 260. In accordance with various embodiments, the actuator is a pneumatic actuator for positioning the needle within a plane. In accordance with various embodiments, the actuator is pneumatically controlled and other components in the entire robotic system 260 is mechanically controlled by one or more servo motors. In accordance with various embodiments, almost all components of the robotic system 260, including the actuator is mechanically controlled by one or more servo motors.

In accordance with various embodiments, the robotic arm 262 of the robotic system 260 is constrained to move along parallel lines, such as for example, in transperineal prostate procedures. In accordance with various embodiments, an additional degree of freedom (in addition to the 6-degrees of freedom) include angular motions so that the needle attached to the robotic arm 262 is maneuvered past the pubic arch area, such as in case of an enlarged prostate gland. In accordance with various embodiments, the robotic system 260 is constrained to move so as to maintain an external Remote Center of Motion (RCM) such that it can approach the same location inside the body through various trajectories. In an RCM model, the robotic mechanism moves in such a fashion that the tool actuated by it always has the trajectory passing through a fixed point relative to the robotic mechanism. For example, for a minimally invasive single port intervention, the RCM may be kept fixed at the entry port into the body and the robotic mechanism may enter it through different angles to advance the tool to different locations inside the body. In accordance with various embodiments, the RCM center may be on surface of the patient's body to facilitate sampling/treating multiple location through only one access puncture/port.

In accordance with various embodiments, an operator may preload multiple needles 280 within the actuator within if a biopsy plan is already determined. In such cases, the biopsy plan includes obtaining sample specimens from all planned locations as described with respect to, for example, FIGS. 4C, 4D, 5A, 5B, 6A, 6B. In such implementation, the robotic arm 262 is configured to acquire multiple samples at once using multiple needles 280. In such a case, the prostate sample may need to be kept in place by using a trans-urethral tube (not shown). It may also be sufficient to only track one of the needles 280 since the prostate gland movement is only along the needle insertion direction and will be equal for all needles being inserted at the same time. As such, a motion correction for a central needle may be sufficient to correct for motion for all the needles 280.

In accordance with various embodiments, the needles 280 may be inserted one at a time. In such configuration, a pre-determined order of needle insertion is used along with the optimized sampling scheme such that the effect of the needle insertion on imaging of the next target locations is minimized. In this implementation, while the actuator does not hold all the needles for insertion at the same time, it holds several needles in a cartridge or end-effector 266 to insert and withdraw one needle at a time. This is done to avoid withdrawing the entire robotic arm 262 across the bore 222.

In accordance with various embodiments, the needle 280 has an RF coil or metamaterial attached to the needle. In accordance with various embodiments, the RF coil or metamaterial is configured to couple to a receive coil chain of the magnetic imaging apparatus 220. This implementation would allow for wireless coupling and the transfer of information to the receive coil network to be digitized by the computer. In accordance with various embodiments, the attached RF coil or metamaterial can increase signal transduction from the tissue surrounding the needle during the insertion, which, in turn, improves the image quality acquired during the scan by the magnetic imaging apparatus 220.

In accordance with various embodiments, the guided robotic system 200 used for guided robotic procedures, such as those described with respect to, for example, FIGS. 4A, 4B, 4C, 4D, 5A, 5B, 5C, 5D, 6A, and 6D, includes an additional configuration that utilizes a nuclear magnetic resonance (NMR) analysis network. In accordance with various embodiments, the NMR analysis network on the robotic system 260 is configured to utilize a higher magnetic field within the bore 222 to perform spectral analysis on the collected biopsy specimens. Since it is known that different tissue types have different NMR spectrums, the type and amount of tissues in each specimen can be characterized quickly, soon after the specimens are acquired. In accordance with various embodiments, the additional NMR information collected and analyzed from the specimens can be used for real-time feedback on the tissue type, providing additional information that may be relevant to the pathology of the biopsy core.

In accordance with various embodiments, the guided robotic system 200 used for guided robotic procedures, such as those described with respect to, for example, FIGS. 4A, 4B, 4C, 4D, 5A, 5B, 5C, 5D, 6A, and 6D, includes an additional configuration that utilizes ultrasound for guidance. In accordance with various embodiments, an apparatus for acquiring ultrasound is external to the guided robotic system 200. In accordance with various embodiments, the apparatus for acquiring ultrasound is integrated in the guided robotic system 200, for example, integrated to the robotic arm 262, near the end-effector 266. In accordance with various embodiments, the guided robotic system 200 supplemented with ultrasound can improve magnetic guidance providing faster imaging updates or for localizing the veins and arteries within the subject during the operation or intervention.

Additional medical procedures, operations, or interventions where the guided robotic system 100 or the guided robotic system 200 uses magnetic imaging technique can include, but not limited to, for example, Transperineal biopsies, Transperineal LDR brachytherapy, Transperineal HDR brachytherapy, Transperineal laser ablation, Transperineal cryoablation, and Transrectal HIFU.

For Transrectal HIFU, in accordance with various embodiments, the robotic system 260 is used to turn the transrectal HIFU transducer about its axis. In accordance with various embodiments, an operator or a physician inserts the transducer first, then moves the patient in the magnetic imaging field of view. In these implementations, the robotic arm 262 is configured to approach through the bore 222 of the magnetic imaging apparatus 220 and latch into the transducer or its holder.

Additional medical procedures, operations, or interventions where the guided robotic system 100 or the guided robotic system 200 uses magnetic imaging technique include breast biopsies. In breast biopsies, the procedure is similar to the prostate biopsy although the direction of insertion maybe different. For example, the robotic system 260 used for breast biopsy can be configured to extend using the one or more mechanical arm portions of the robotic arm 262 to reach the target portions of the breast around the magnetic imaging apparatus 220, instead of through the bore 222. The configuration is suitable for breast biopsy particular, where the needle 280 is inserted from the side of the breast.

Additional medical procedures, operations, or interventions where the guided robotic system 100 or the guided robotic system 200 uses magnetic imaging technique include deep brain stimulation (DBS). For DBS, the planning beforehand, e.g. before the procedure or intervention, is done to ensure that the needle trajectory does not go through any critical structure. In accordance with various embodiments, the critical structures are segmented, identified, or marked beforehand either automatically or manually. These structures can then be overlaid on the live image during the procedure. During live guidance, the image will be acquired to ensure that the needle 280 is inserted to the accurate location under direct visualization such that no critical structures are damaged or violated. In accordance with various embodiments, to minimize the complexity, a RCM model may be used once an entry point is selected for the entry into the brain.

Additional medical procedures, operations, or interventions where the guided robotic system 100 or the guided robotic system 200 uses magnetic imaging technique include brain biopsies. In accordance with various embodiments, brain biopsies are conducted using the projected needle trajectory, which is displayed to the operator on live guidance panel, for example, as shown in FIG. 3A. Upon reviewing the information on live guidance panel of the middle panel 320, that operator can decide to initiate insertion of the needle. In accordance with various embodiments, the guided robotic system 200 is configured to record the target location of the brain. In accordance with various embodiments, the operator reviews the acquired images of the target location of the brain and enter the pathology findings for each findings along with their respective location within the images.

Additional medical procedures, operations, or interventions where the guided robotic system 100 or the guided robotic system 200 uses magnetic imaging technique include liver and kidney biopsies. In accordance with various embodiments, liver and kidney biopsies include insertion at one entry point to obtain the specimen. In accordance with various embodiments, to minimize the complexity, a remote center or motion (RCM) model may be used once an entry point is selected for the entry into the brain.

Additional medical procedures, operations, or interventions where the guided robotic system 100 or the guided robotic system 200 uses magnetic imaging technique include lung biopsies. In accordance with various embodiments, lung biopsies include insertion of a tube through the trachea utilizing a robotic system.

In accordance with various embodiments as described herein, the guided robotic system 100 or the guided robotic system 200 can be utilized for medical procedures, operations, or interventions for insertion of a stent, for example, a coronary stent or brain stent. In accordance with various embodiments as described herein, the guided robotic system 100 or the guided robotic system 200 can be used for intensity modulated radiation treatment guidance.

Figure 7:
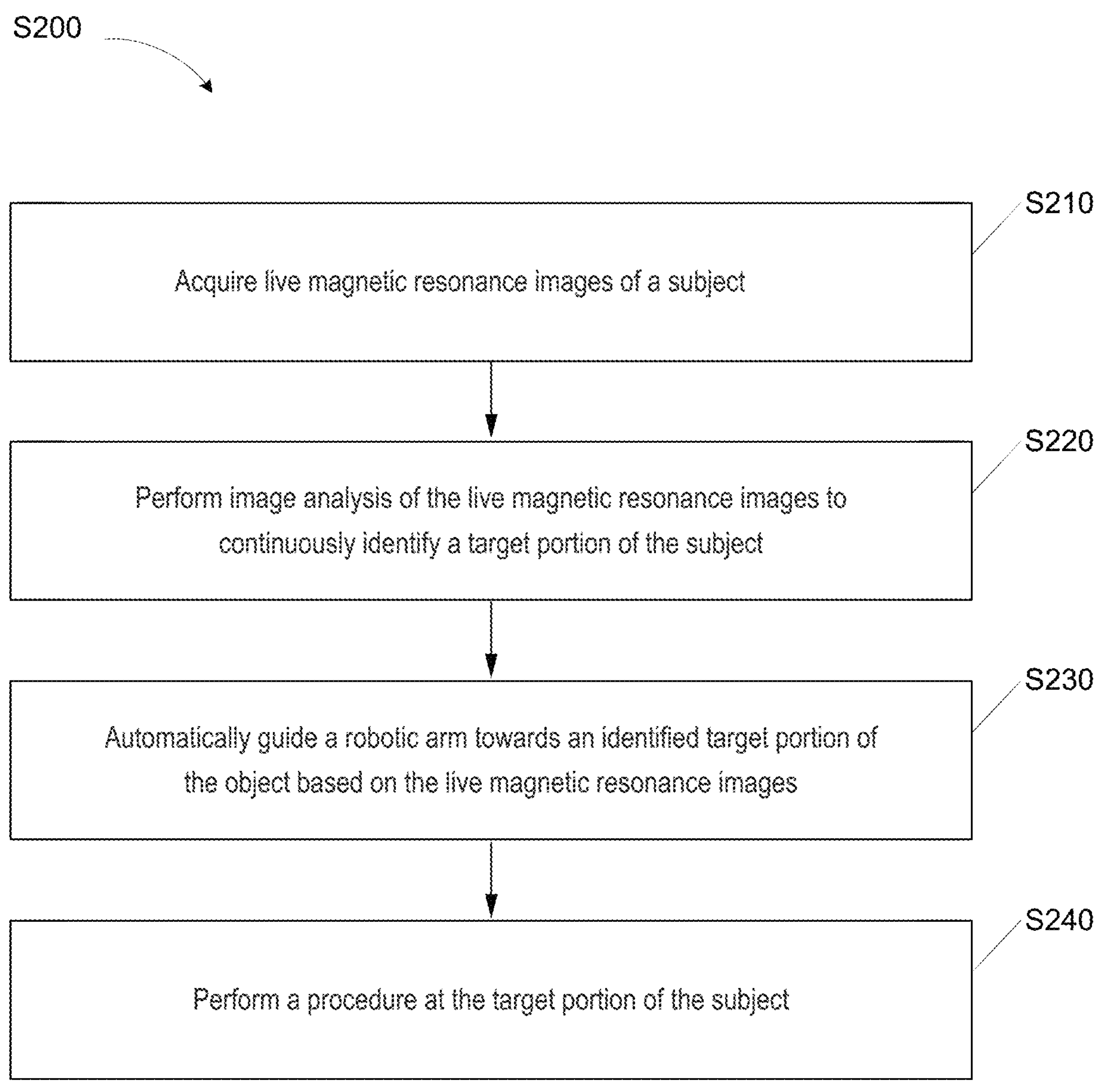
FIG. 7 is a flowchart for a method of using a guided robotic system, according to various aspects of the present disclosure.

FIG. 7 is a flowchart for an example method S200 of using the guided robotic system 200, according to various embodiments. As shown in FIG. 7, the method S200 includes at step S210 acquiring magnetic resonance images of a subject. In accordance with various embodiments, the acquiring of the images of the subject includes acquiring one or more target anatomical parts of the subject or the patient. In accordance with various embodiments, the magnetic resonance images are acquired from a magnetic resonance imaging apparatus, such as the magnetic imaging apparatus 200 or an external source. In accordance with various embodiments, the magnetic resonance images are acquired from an external source, such as a physician, a patient, a user or an operator.

As shown in FIG. 7, the method S200 includes at step S220 performing image analysis of the live magnetic resonance images to continuously identify a target portion of the subject. In accordance with various embodiments, the acquired magnetic resonance images are automatically uploaded into a computer system, such as the computer system 240, for analysis via one or more processes including, but not limited to, artificial intelligence (AI), machine learning, image or signal denoising, segmentation algorithms, objects and boundary identification, image registration, adaptive intensity correction, and pattern recognition, etc. In accordance with various embodiments, the acquired magnetic resonance images are manually analyzed and entered by a physician or an operator into a computer system, such as the computer system 240, which is used to automatically identify a portion of the subject from the analyzed images.

At step S230, the method S200 includes automatically guiding (via automatic guidance) a robotic arm, such as the robotic arm 262, to an identified target portion of the subject based on the live magnetic resonance images. In accordance with various embodiments, the automatic guidance includes guiding the robotic arm in real-time or near real-time based on analysis of continuously acquired magnetic resonance images of the target portion of the subject. In accordance with various embodiments, the automatic guidance includes self-correction via image analysis. In accordance with various embodiments, the automatic guidance includes occasional interventions by a physician or an operator to correct the trajectory of the robotic arm based on acquired magnetic resonance images. In accordance with various embodiments, the automatic guidance includes occasional interventions by a physician or an operator to alter the trajectory of the robotic arm based on acquired magnetic resonance images in order to perform alternative or additional medical procedures.

In accordance with various embodiments of the method S200, the robotic arm is configured for movements in 6-degrees of freedom, such as the robotic arm 262. In accordance with various embodiments, the robotic arm includes one or more mechanical arm portions that are connected in a configuration to allow the robotic arm to move, rotate, or swivel in 6-degrees of freedom. In accordance with various embodiments, the robotic arm is configured for accessing various anatomical parts of the subject.

In accordance with various embodiments of the method S200, no critical structures are damaged during the needle insertion by the robotic arm 262. For example, in accordance with various embodiments of a prostate biopsy, the guided robotic system 200 is configured such that the needle, which is attached to the robotic arm 262 being inserted into the target portion of the subject, avoids passing through urethra or into the bladder. In accordance with various embodiments of brachytherapy, the needle does not penetrate beyond the prostate into the bladder and does not ablate the rectum or the bladder.

In accordance with various embodiments the method S200, acquired live magnetic resonance images are displayed within a graphical user interface (GUI) that includes functional buttons for controlling the procedure. In accordance with various embodiments, acquired live magnetic resonance images comprise a high resolution image portion near a needle inserted during the procedure and a lower resolution image portion farther away from the needle. In accordance with various embodiments, the method S200 further includes correcting acquired live magnetic resonance images for motion during the performing of the procedure. In accordance with various embodiments, the method S200 further includes correcting acquired live magnetic resonance images for motion during insertion of the needle. In accordance with various embodiments, the method S200 further includes overriding existing action to manually correct for the motion. In accordance with various embodiments, the method S200 further includes manually advancing the robotic arm by controlling the GUI using a touch input, a mouse input or a joystick input. In accordance with various embodiments, the method S200 further includes performing automatic segmentation to capture the location of the needle after extracting the specimen, withdrawing the needle, and advancing the needle to a next target location.

At step S240, the method S200 includes performing a procedure at the target portion of the subject. In accordance with various embodiments, the method S200 includes performing a suitable medical procedure including for example, but not limited to, transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance, etc. In accordance with various embodiments, performing a procedure includes extracting a specimen, for example, for biopsy.

Figure 8:
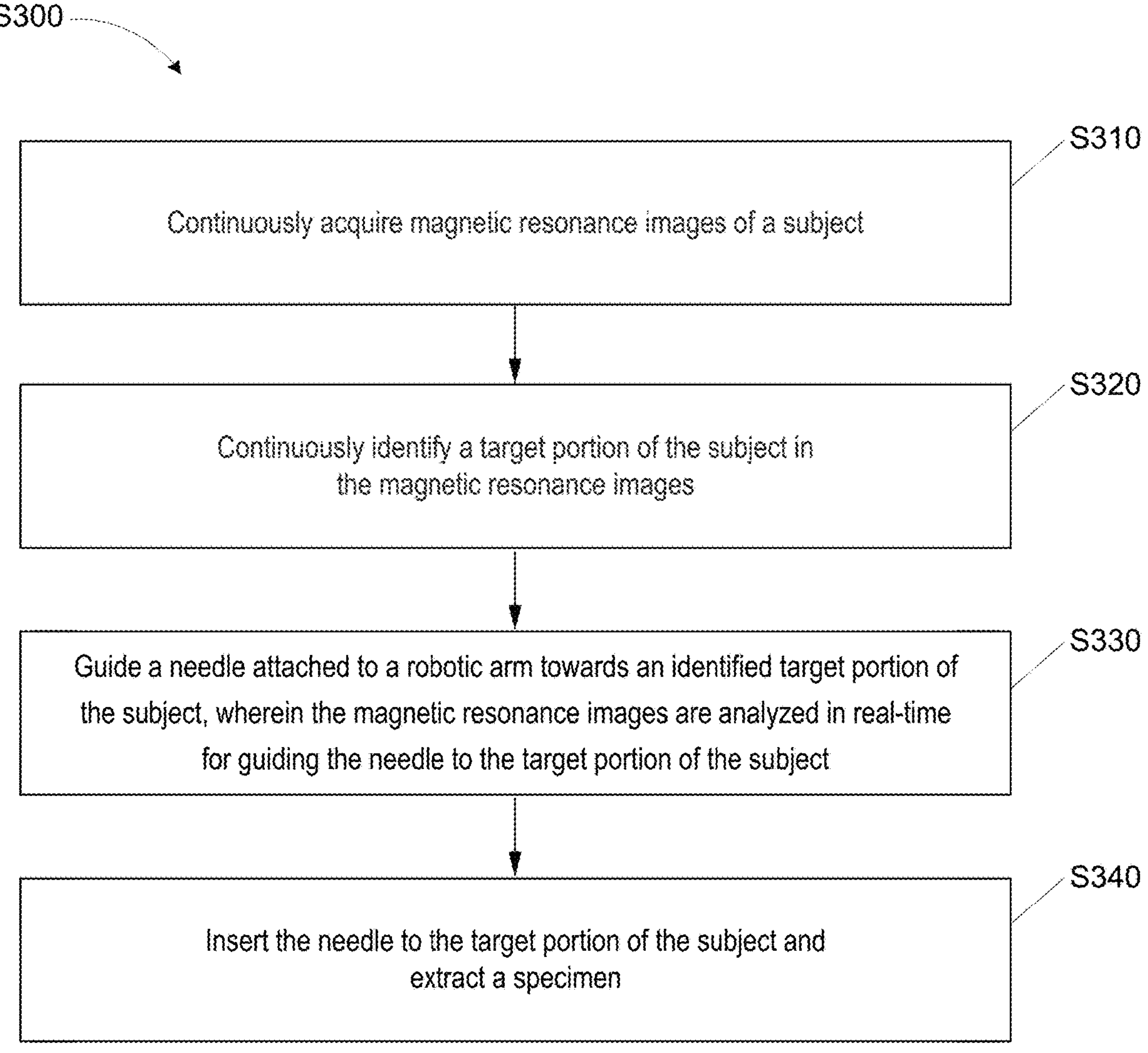
FIG. 8 is another flowchart for a method of using a guided robotic system, according to various aspects of the present disclosure.

FIG. 8 is a flowchart for an example method S300 of using the guided robotic system 200, according to various embodiments. As shown in FIG. 8, the method S300 includes at step S310 continuously acquiring magnetic resonance images of a subject. In accordance with various embodiments, the acquiring of the images of the subject includes acquiring one or more target anatomical parts of the subject or the patient. In accordance with various embodiments, the magnetic resonance images are acquired from a magnetic resonance imaging apparatus, such as the magnetic imaging apparatus 100 or 200, or an external source. In accordance with various embodiments, the magnetic resonance images are acquired from an external source, such as a physician, a patient, a user or an operator.

At step S320, the method S300 includes continuously identifying a target portion of the subject in the magnetic resonance images. In accordance with various embodiments, the acquired magnetic resonance images are automatically uploaded into a computer system, such as the computer system 240, for analysis via one or more processes including, but not limited to, artificial intelligence (AI), before identification of the target portion. In accordance with various embodiments, the acquired magnetic resonance images are manually analyzed and entered by a physician or an operator into a computer system, such as the computer system 240, which is used to automatically identify a portion of the subject from the analyzed images.

At step S330, the method S300 includes guiding a robotic arm, such as the robotic arm 262, towards an identified target portion of the subject, wherein the magnetic resonance images are analyzed in real-time for guiding the robotic arm to the portion of the subject. In accordance with various embodiments, the continuously acquired magnetic resonance images are analyzed in real-time or near real-time to continuously identify the target portion of the subject. In accordance with various embodiments, the guiding of the robotic arm includes self-correction via image analysis. In accordance with various embodiments, the guiding of the robotic arm includes occasional interventions by a physician or an operator to correct the trajectory of the robotic arm based on the continuously acquired magnetic resonance images. In accordance with various embodiments, the guiding of the robotic arm includes occasional interventions by a physician or an operator to alter the trajectory of the robotic arm based on the continuously acquired magnetic resonance images in order to perform alternative or additional medical procedures.

At step S340, the method S300 includes inserting the needle to the target portion of the subject and extracting a specimen. During the insertion, no critical structures are damaged during the needle insertion by the robotic arm 262. For example, in accordance with various embodiments of a prostate biopsy, the guided robotic system 200 is configured such that the needle, which is attached to the robotic arm 262 being inserted into the target portion of the subject, avoids passing through the urethra or into the bladder. In accordance with various embodiments of brachytherapy, the needle does not penetrate beyond the prostate into bladder and does not ablate rectum or bladder.

In accordance with various embodiments of the method S300, continuously acquired live magnetic resonance images are displayed within a graphical user interface (GUI) that includes functional buttons for controlling during insertion of the needle. In accordance with various embodiments, continuously acquired live magnetic resonance images comprise a high resolution image portion near the needle and a lower resolution image portion farther away from the needle. In accordance with various embodiments, the method S300 further includes automatically correcting the continuously acquired live magnetic resonance images to compensate for motion blurring during insertion of the needle. In accordance with various embodiments, the method S300 further includes automatically correcting a trajectory of the needle during the insertion based on corrected acquired live magnetic resonance images. In accordance with various embodiments, the method S300 further includes overriding existing guided trajectory to manually correct for the motion blur. In accordance with various embodiments, the method S300 further includes manually advancing the robotic arm by controlling the GUI using a touch input, a mouse input or a joystick input. In accordance with various embodiments, the method S300 further includes performing automatic segmentation to capture the location of the needle after extracting the specimen, withdrawing the needle; and advancing the needle to a next target location. In accordance with various embodiments, the guiding of the needle attached to the robotic arm towards the identified target portion of the subject includes guiding through a bore at the center of a magnetic imaging apparatus configured for continuously acquiring magnetic resonance images.

In accordance with various embodiments of step S340, the extracted specimen is for analysis in a medical procedure, such as for example, but not limited to, transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance, etc.

Figure 9:
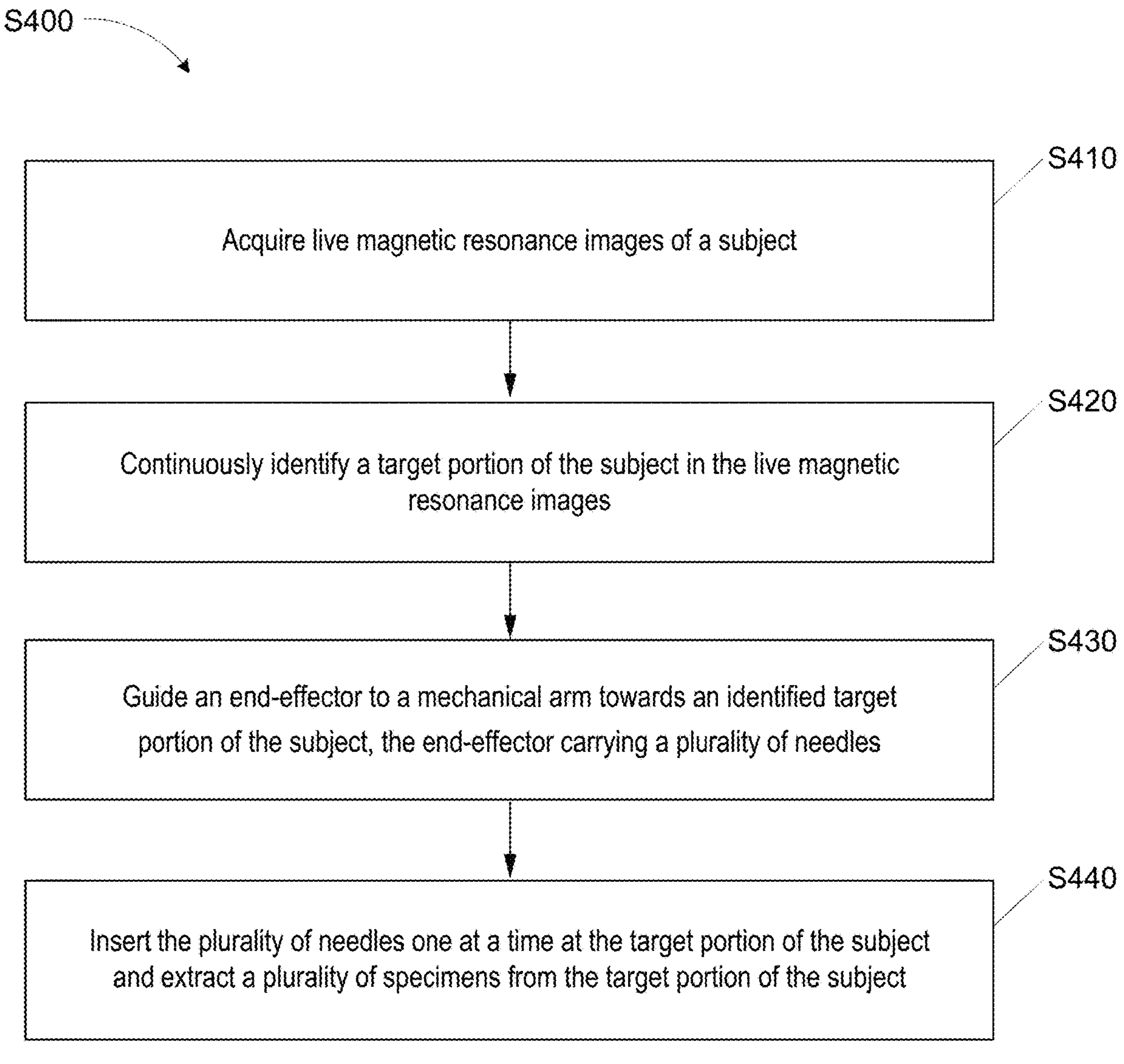
FIG. 9 is another flowchart for a method of using a guided robotic system, according to various aspects of the present disclosure.

FIG. 9 is a flowchart for an example method S400 of using the guided robotic system 200, according to various embodiments. As shown in FIG. 9, the method S400 includes at step S410 acquiring live magnetic resonance images of a subject. In accordance with various embodiments, the acquiring of the live magnetic resonance images of the subject includes acquiring one or more target anatomical parts of the subject or the patient. In accordance with various embodiments, the live magnetic resonance images are acquired from a magnetic resonance imaging apparatus, such as the magnetic imaging apparatus 100 or 200.

At step S420, the method S400 includes continuously identifying a target portion of the subject in the live magnetic resonance images. In accordance with various embodiments, the acquired live magnetic resonance images are automatically uploaded into a computer system, such as the computer system 240, for analysis via one or more processes including, but not limited to, artificial intelligence (AI), before identification of the target portion. In accordance with various embodiments, the acquired live magnetic resonance images are manually analyzed and entered by a physician or an operator into a computer system, such as the computer system 240, which is used to automatically identify a portion of the subject from the analyzed images.

At step S430, the method S300 includes guiding an end-effector attached to a mechanical arm towards an identified target portion of the subject. In accordance with various embodiments, the end-effector is configured to carry a plurality of needles.

At step S440, the method S300 includes inserting the plurality of needles one at a time or sequentially at the target portion of the subject and extracting a plurality of specimens from the target portion of the subject. In accordance with various embodiments of the step S440, no critical structures of the subject are damaged during the needle insertion by the robotic arm 262. For example, in accordance with various embodiments of a prostate biopsy, the guided robotic system 200 is configured such that the needle, which is attached to the robotic arm 262 being inserted into the target portion of the subject, avoids passing through the urethra or into the bladder. In accordance with various embodiments of brachytherapy, the needle does not penetrate beyond the prostate into bladder and does not ablate rectum or bladder.

In accordance with various embodiments of the method S400, acquired live magnetic resonance images are displayed within a graphical user interface (GUI) that includes functional buttons for controlling during insertion of the plurality of needles. In accordance with various embodiments, acquired live magnetic resonance images comprise a high resolution image portion near an inserted needle and a lower resolution image portion farther away from the inserted needle. In accordance with various embodiments, the method S400 further includes automatically correcting the acquired live magnetic resonance images to compensate for motion blurring during insertion of the plurality of needles. In accordance with various embodiments, the method S400 further includes automatically correcting a trajectory of an inserted needle during the insertion based on corrected acquired live magnetic resonance images. In accordance with various embodiments, the method S400 further includes overriding existing guided trajectory to manually correct for the motion blur. In accordance with various embodiments, the method S400 further includes manually advancing the mechanical arm by controlling the GUI using a touch input, a mouse input or a joystick input. In accordance with various embodiments, the method S400 further includes performing automatic segmentation to capture the location of an inserted needle after extracting the specimen, withdrawing the inserted needle, and inserting a further needle at a next location. In accordance with various embodiments, the guiding of the end-effector attached to the mechanical arm towards the identified target portion of the subject includes guiding through a bore at the center of a single-sided magnetic imaging apparatus configured for continuously acquiring magnetic resonance images.

In accordance with various embodiments of the step S440, the plurality of extracted specimens are for analyzed in one or more medical procedures, such as for example, but not limited to, transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance, etc.

Figures 10, 11:
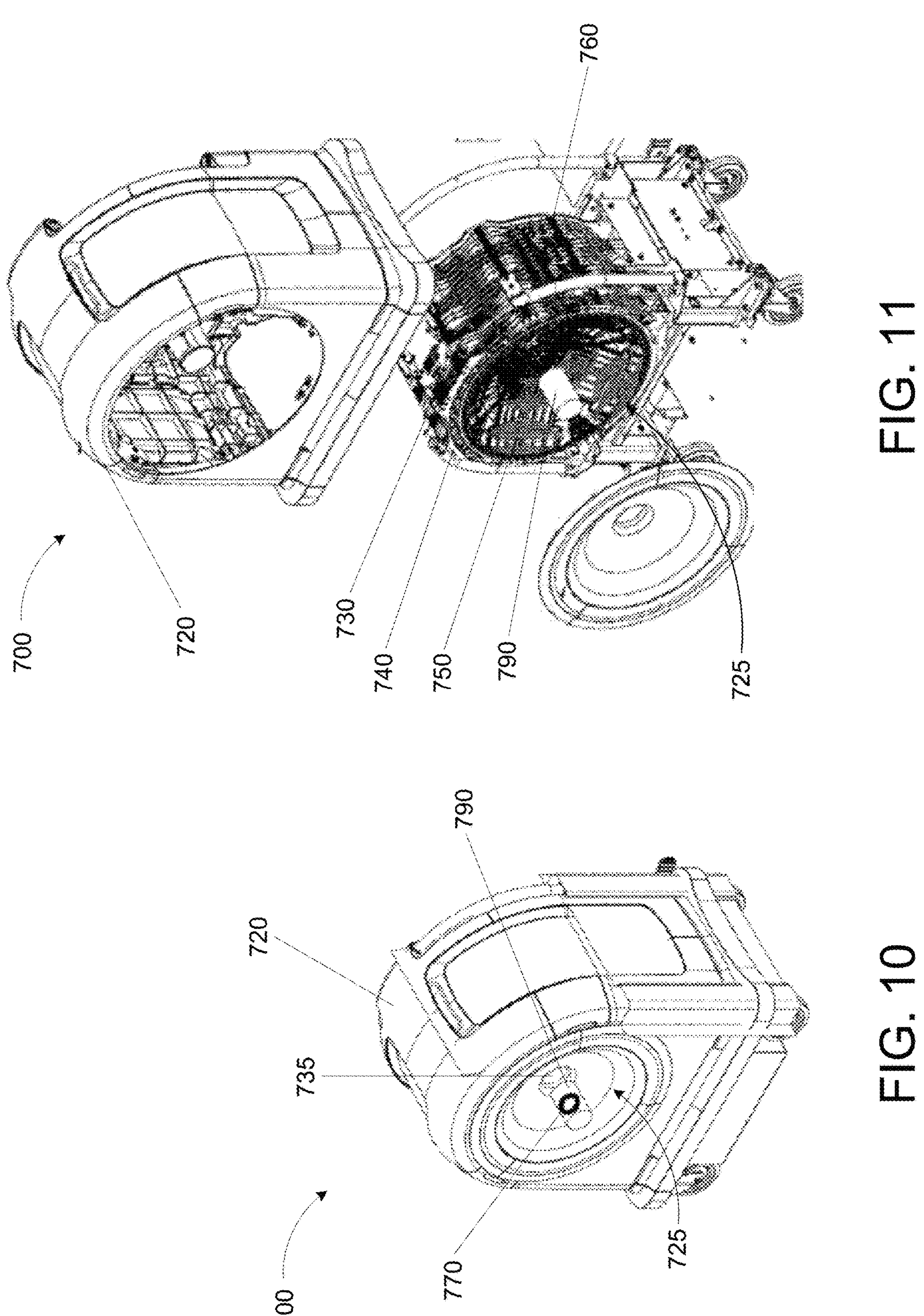
FIG. 10 is a schematic illustration of a magnetic resonance imaging system, according to various aspects of the present disclosure.
FIG. 11 is an exploded, perspective view of the magnetic resonance imaging system shown in FIG. 10, according to various aspects of the present disclosure.

FIGS. 10-14 depict an magnetic resonance imaging system 700. As shown in FIGS. 10 and 11, the magnetic resonance imaging system 700 includes a housing 720. The housing 720 includes a front surface 725. In accordance with various embodiments, the front surface 725 can be a concave front surface. In accordance with various embodiments, the front surface 725 can be a recessed front surface.

Figures 12, 13:
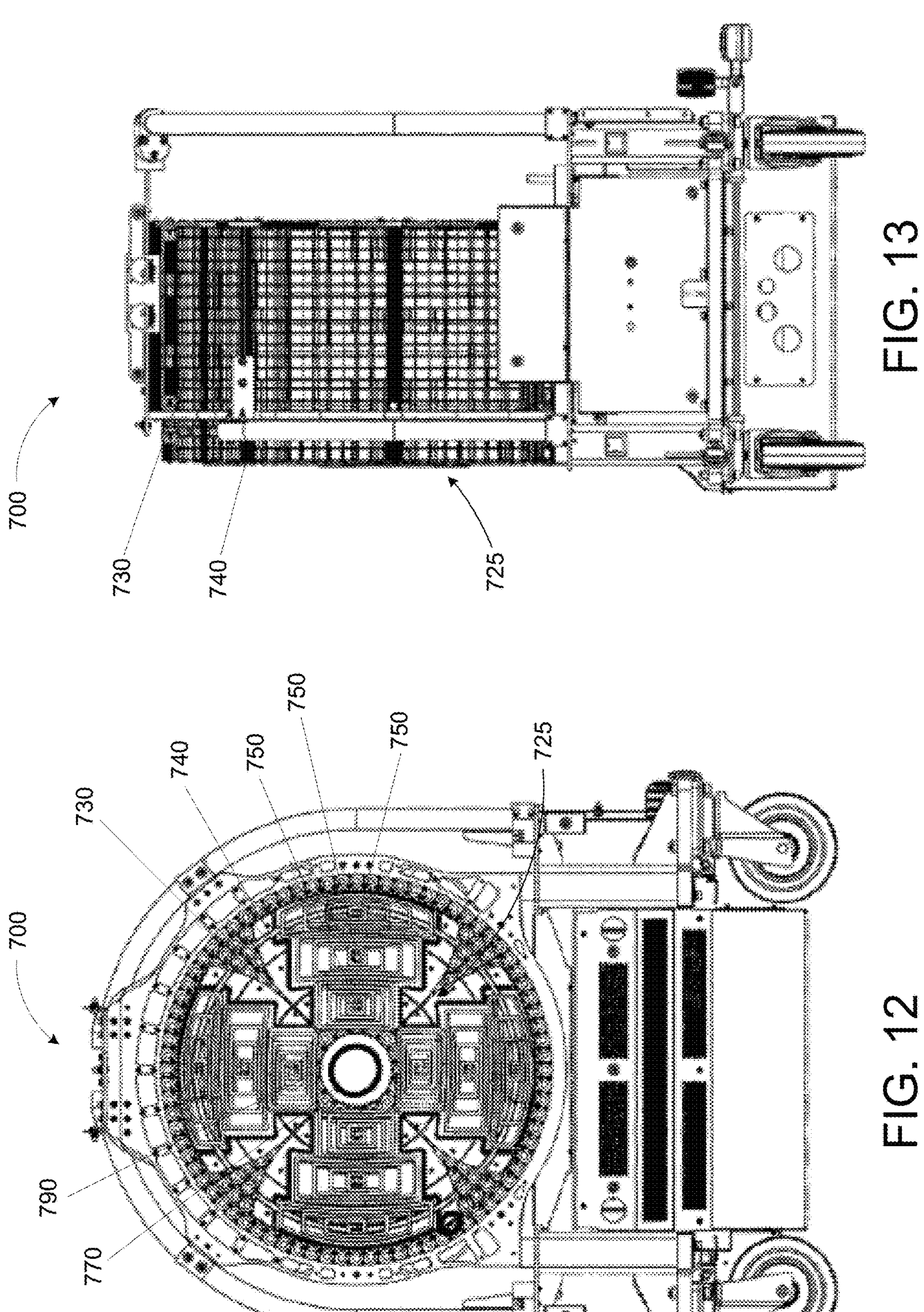
FIG. 12 is an elevation view of the magnetic resonance imaging system shown in FIG. 10, according to various aspects of the present disclosure.
FIG. 13 is an elevation view of the magnetic resonance imaging system shown in FIG. 10, according to various aspects of the present disclosure.

As shown in FIGS. 10 and 11, the housing 720 includes a permanent magnet 730, a radio frequency transmit coil 740, a gradient coil set 750, an electromagnet 760, and a radio frequency receive coil 770. As shown in FIGS. 12 and 13, the permanent magnet 730 can include a plurality of magnets disposed in an array configuration. The plurality of magnets forming the permanent magnet 730 are illustrated to cover an entire surface as shown in the front elevation view of FIG. 12 and illustrated as bars in a horizontal direction as shown in the side election view of FIG. 13. Referring primarily to FIG. 10, the main permanent magnet array can include at least one access aperture 735 for accessing the patient from multiple sides of the system.

In accordance with various embodiments, the permanent magnet 730 provides a static magnetic field in a region of interest 790. In accordance with various embodiments, the permanent magnet 730 can include a plurality of cylindrical permanent magnets in parallel configuration as shown in FIGS. 12 and 13. In accordance with various embodiments, the permanent magnet 730 can include any suitable magnetic materials, including but not limited, to rare-earth based magnetic materials, such as for example, Nd-based magnetic materials, and the like. As shown in FIG. 10, the main permanent magnet can include at least one access aperture 735 for accessing the patient from the opposite side of the system through the body of the magnetic imaging system 700.

Figure 14:
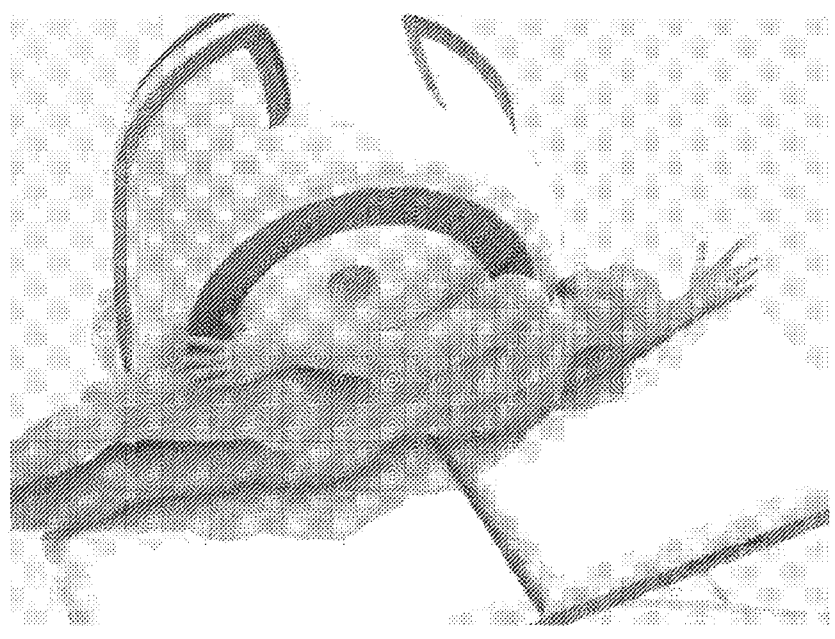
FIG. 14 illustrates exemplary positioning of a patient for imaging by a magnetic resonance imaging system for certain surgical procedures and interventions, according to various aspects of the present disclosure.

In accordance with various embodiments, using the magnetic resonance imaging system illustrated in FIG. 14, a patient can be positioned in any number of different positions depending on the type of anatomical scan desired. FIG. 14 illustrates an example position for when the abdomen-region is scanned. The patient can be laid on a surface at a lateral position. As illustrated, for the abdominal scan, a patient can be positioned to lay sideways facing the bore, with the arm closest to the table stretched out and the other at the side of the body. The abdomen region can be positioned such that it is directly in front of the bore. A robotic system can be placed on the other side of the magnetic resonance imaging system, such that the robotic system is away from the patient. A robotic arm of the robotic system can reach through the access aperture in the magnetic resonance imaging system to perform a procedure on the patient. In this example setup, there is the robotic system, then the magnetic resonance imaging system, and then the patient. This example setup keeps the patient close to the magnetic resonance imaging system and only allows the arm of the robotic system to reach toward the patient through an access aperture, which keeps the motors of the robotic system away from the magnetic resonance imaging system reducing interference with the magnetic resonance imaging. In other instances, the arm of the robotic system may reach around the side of the magnetic resonance imaging system to reach the patient. In both instances, the magnetic resonance imaging system is intermediate the patient and proximal portion of the robotic arm.

EXAMPLES

Example 1—A guided robotic system, comprising: a magnetic imaging apparatus for continuously acquiring magnetic resonance images of a subject; a robotic arm, and a computer system for analyzing the magnetic resonance images and identifying a portion of the subject, wherein the magnetic resonance images are analyzed in real-time for guiding the robotic arm to the portion of the subject.

Example 2—The system of Example 1, wherein the robotic arm is attached to a component configured for drug delivery.

Example 3—The system of any one of Examples 1 and 2, wherein the robotic arm is configured for inserting a needle into the portion of the subject for extracting a specimen.

Example 4—The system of any one of Examples, 1, 2, and 3, wherein the robotic arm is configured for placing a stent into the portion of the subject.

Example 5—The system of any one of Examples 1, 2, 3, and 4, wherein the robotic arm is attached to a needle configured for removing a sample from the portion of the subject.

Example 6—The system of any one of Examples 1, 2, 3, 4, and 5, wherein the robotic arm is configured for removing the identified portion by cutting the portion of the subject.

Example 7—The system of any one of Examples 1, 2, 3, 4, 5, and 6, wherein the robotic arm is attached to an end-effector containing a plurality of needles.

Example 8—The system of any one of Examples 1, 2, 3, 4, 5, 6, and 7, wherein the robotic arm is attached to an end-effector configured for carrying one or more stents.

Example 9—The system of any one of Examples 1, 2, 3, 4, 5, 6, 7, and 8, wherein the robotic arm is attached to an end-effector configured for carrying one or more brachytherapy seeds.

Example 10—The system of any one of Examples 1, 2, 3, 4, 5, 6, 7, 8, and 9, wherein the robotic arm is configured for extracting a specimen for examination in a medical procedure from the list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

Example 11—A method of using a guided robotic system, the method comprising: acquiring live magnetic resonance images of a subject; performing image analysis of the live magnetic resonance images to continuously identify a target portion of the subject; automatically guiding a robotic arm towards an identified target portion of the subject based on the live magnetic resonance images; and performing a procedure at the target portion of the subject.

Example 12—The method of Example 11, wherein acquired live magnetic resonance images are displayed within a graphical user interface (GUI) that includes functional buttons for controlling the procedure.

Example 13—The method of any one of Examples 11 and 12, wherein acquired live magnetic resonance images comprise a high resolution image portion near a needle inserted during the procedure and a lower resolution image portion farther away from the needle.

Example 14—The method of any one of Examples 11, 12, and 13, further comprising: correcting acquired live magnetic resonance images for patient motion during the performing of the procedure.

Example 15—The method of any one of Examples 11, 12, 13, and 14, further comprising: correcting acquired live magnetic resonance images for motion artifacts during insertion of the needle.

Example 16—The method of any one of Examples 11, 12, 13, 14, and 15, further comprising: overriding existing action to manually correct for the patient motion.

Example 17—The method of any one of Examples 11, 12, 13, 14, 15, and 16, further comprising: manually advancing the robotic arm by controlling the GUI using a touch input, a mouse input or a joystick input.

Example 18—The method of any one of Examples 11, 12, 13, 14, 15, 16, and 17, further comprising: providing a needle attached to the robotic arm, performing automatic segmentation to capture location of the needle; withdrawing the needle; and advancing the needle to a next target location.

Example 19—The method of any one of Examples 11, 12, 13, 14, 15, 16, 17, and 18, wherein the procedure includes one from the list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

Example 20—A method of using a guided robotic system, the method comprising: continuously acquiring magnetic resonance images of a subject; continuously identifying a target portion of the subject in the magnetic resonance images; guiding a needle attached to a robotic arm towards an identified target portion of the subject, wherein the magnetic resonance images are analyzed in real-time for guiding the needle to the target portion of the subject; and inserting the needle to the target portion of the subject and extracting a specimen.

Example 21—The method of Example 20, wherein continuously acquired live magnetic resonance images are displayed within a graphical user interface (GUI) that includes functional buttons for controlling during insertion of the needle.

Example 22—The method of any one of Examples 20 and 21, wherein continuously acquired live magnetic resonance images comprise a high resolution image portion near the needle and a lower resolution image portion farther away from the needle.

Example 23—The method of any one of Examples 20, 21, and 22, further comprising: automatically correcting the continuously acquired live magnetic resonance images to compensate for motion blurring during insertion of the needle.

Example 24—The method of Example 23, further comprising: automatically correcting a trajectory of the needle during the insertion based on corrected acquired live magnetic resonance images.

Example 25—The method of Example 23, further comprising: overriding existing guided trajectory to manually correct for the motion blur.

Example 26—The method of any one of Examples 20, 21, 22, 23, 24, and 25, further comprising: manually advancing the robotic arm by controlling the GUI using a touch input, a mouse input or a joystick input.

Example 27—The method of any one of Examples 20, 21, 22, 23, 24, 25, and 26, further comprising: performing automatic segmentation to capture location of the needle; withdrawing the needle; and advancing the needle to a next target location.

Example 28—The method of any one of Examples 20, 21, 22, 23, 24, 25, 26, and 27, wherein extracted specimen is examined in a medical procedure from the list consisting of transperineal biopsy, transperineal LDR brachytherapy, transperineal HDR brachytherapy, transperineal laser ablation, transperineal cryoablation, transrectal HI FU, breast biopsies, deep brain stimulation (DBS), brain biopsy, liver biopsy, kidney biopsy, lung biopsy, coronary stent insertion, brain stent insertion, and intensity modulated radiation treatment guidance.

Example 29—The method of any one of Examples 20, 21, 22, 23, 24, 25, 26, 27, and 28, wherein the guiding further includes guiding the needle through a bore at the center of a magnetic imaging apparatus configured for continuously acquiring magnetic resonance images.

Example 30—A method of using a guided system, the method comprising: acquiring live magnetic resonance images of a subject; continuously identifying a target portion of the subject in the live magnetic resonance images; guiding an end-effector attached to a mechanical arm towards an identified target portion of the subject, the end-effector carrying a plurality of needles; and inserting the plurality of needles one at a time at the target portion of the subject and extracting a plurality of specimens from the target portion of the subject.

Example 31—The method of Example 30, wherein acquired live magnetic resonance images are displayed within a graphical user interface (GUI) that includes functional buttons for controlling during insertion of the plurality of needles.

Example 32—The method of any one of Examples 30 and 31, wherein acquired live magnetic resonance images comprise a high resolution image portion near an inserted needle and a lower resolution image portion farther away from the inserted needle.

Example 33—The method of any one of Examples 30, 31, and 32, further comprising: automatically correcting the acquired live magnetic resonance images to compensate for motion blurring during insertion of the plurality of needles.

Example 34—The method of Example 33, further comprising: automatically correcting a trajectory of an inserted needle during the insertion based on corrected acquired live magnetic resonance images.

Example 35—The method of any one of Examples 30, 31, 32, 33, and 34, further comprising: overriding existing guided trajectory to manually correct for the motion blur.

Example 36—The method of any one of Examples 30, 31, 32, 33, 34, and 35, further comprising: manually advancing the mechanical arm by controlling the GUI using a touch input, a mouse input or a joystick input.

Example 37—The method of any one of Examples 30, 31, 32, 33, 34, 35, and 36, further comprising: performing automatic segmentation to capture location of an inserted needle; withdrawing the inserted needle; and inserting a further needle at a next location.

Example 38—The method of any one of Examples 30, 31, 32, 33, 34, 35, 36, and 37, wherein extracted specimens are examined in one or more medical procedures from the list consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

Example 39—The method of any one of Examples 30, 31, 32, 33, 34, 35, 36, 37, and 38, wherein the guiding of the end-effector attached to the mechanical arm towards the identified target portion of the subject includes guiding through a bore at the center of a single-sided magnetic imaging apparatus configured for continuously acquiring magnetic resonance images.

Example 40—A guided robotic system, comprising an imaging apparatus for real-time imaging of a subject; a computer system for analyzing images in real-time; and a robotic system comprising a robotic arm, wherein the robotic system is configured to guide the robotic arm during a surgical procedure based on real-time analysis of the images, and wherein the robotic arm comprises: a proximal end and a distal end configured to hold a robotic surgical tool, wherein the imaging apparatus is positioned intermediate the proximal end of the robotic arm and the subject during the surgical procedure.

Example 41—The system of Example 40, wherein the distal end of the robotic arm is attached to a component configured for drug delivery.

Example 42—The system of any one of Examples 40 and 41, wherein the distal end of the robotic arm is configured for inserting a needle into the subject for extracting a specimen.

Example 43—The system of any one of Examples 40, 41, and 42, wherein the robotic arm is configured for placing a stent into the subject.

Example 44—The system of any one of Examples 40, 41, 42, and 43, wherein the robotic arm is attached to a needle configured for removing a sample from the subject.

Example 45—The system of any one of Examples 40, 41, 42, 43, and 44, wherein the robotic arm is attached to an ablation tool.

Example 46—The system of any one of Examples 40, 41, 42, 43, 44, and 45, wherein the distal end of the robotic arm is attached to an end-effector containing a plurality of needles.

Example 47—The system of any one of Examples 40, 41, 42, 43, 44, 45, and 46, wherein the distal end of the robotic arm is attached to an end-effector configured for carrying one or more stents.

Example 48—The system of any one of Examples 40, 41, 42, 43, 44, 45, 46, and 47, wherein the distal end of the robotic arm is attached to an end-effector configured for carrying one or more brachytherapy seeds.

Example 49—The system of any one of Examples 40, 41, 42, 43, 44, 45, 46, 47, and 48, wherein the robotic arm is configured for extracting a specimen for examination in a medical procedure from the list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

Example 50—The system of any one of Examples 40, 41, 42, 43, 44, 45, 46, 47, 48, and 49, wherein the robotic arm is configured to extend through a bore in the imaging apparatus to position the distal end of the robotic arm proximate to the subject.

Example 51—The system of any one of Examples 40, 41, 42, 43, 44, 45, 46, 47, 48, 49, and 50, wherein the robotic arm comprises a motor, and wherein the imaging apparatus comprises an active noise cancellation module configured to: detect noise generated by the motor; and remove detected noise from the acquired signals.

Example 52—The system of any one of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, and 51, wherein the imaging apparatus is a single-sided magnetic resonance imaging apparatus having a bore at its center.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion, or housing, of the surgical instrument. The term "proximal" refers to the portion closest to the clinician and/or to the robotic arm and the term "distal" refers to the portion located away from the clinician and/or from the robotic arm. It will be further appreciated that, for convenience and clarity, spatial terms such as "vertical", "horizontal", "up", and "down" may be used herein with respect to the drawings. However, robotic surgical tools are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A guided robotic system, comprising:

a magnetic resonance imaging apparatus for continuously acquiring magnetic resonance images of a subject within a magnetic region of the magnetic resonance imaging apparatus;

a robotic arm; and a computer system for analyzing the magnetic resonance images and identifying a portion of the subject, wherein the magnetic resonance images are analyzed in real-time for guiding the robotic arm to the portion of the subject within the magnetic region;

wherein the magnetic resonance imaging apparatus is positioned intermediate a proximal end of the robotic arm and the subject during a surgical procedure;

wherein the robotic arm is configured to extend from the proximal end of the robotic arm and through a bore in the magnetic resonance imaging apparatus to position a distal end of the robotic arm outside of the bore, proximate to the subject, and within the magnetic region of the magnetic resonance imaging apparatus.

2. The system of claim 1, wherein the robotic arm is attached to an end effector configured for drug delivery.

3. The system of claim 1, wherein the robotic arm is configured for inserting a needle into the portion of the subject for extracting a specimen.

4. The system of claim 1, wherein the robotic arm is configured for placing a stent into the portion of the subject.

5. The system of claim 1, wherein the robotic arm is configured for removing the identified portion by cutting the portion of the subject.

6. The system of claim 1, wherein the robotic arm is configured for extracting a specimen for examination in a medical procedure from a list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

7. A method of using a guided robotic system, the method comprising:

acquiring live magnetic resonance images of a subject via a magnetic resonance imaging apparatus;

performing image analysis of the live magnetic resonance images to continuously identify a target portion of the subject within a magnetic region of the magnetic resonance imaging apparatus;

automatically guiding a robotic arm towards an identified target portion of the subject within the magnetic region based on the live magnetic resonance images, wherein the robotic arm is configured to extend from a proximal end of the robotic arm and through a bore in the magnetic resonance imaging apparatus to position a distal end of the robotic arm outside of the bore, proximate to the subject, and within the magnetic region, wherein the magnetic resonance imaging apparatus is positioned intermediate the proximal end of the robotic arm and the subject during a surgical procedure; and performing the surgical procedure at the target portion of the subject.

8. A guided robotic system, comprising:

a magnetic resonance imaging apparatus for real-time imaging of a subject within a magnetic region of the magnetic resonance imaging apparatus;

a computer system for analyzing images in real-time; and a robotic system comprising a robotic arm, wherein the robotic system is configured to guide the robotic arm during a surgical procedure based on real-time analysis of the images, and wherein the robotic arm comprises:

a proximal end; and a distal end configured to hold a robotic surgical tool;

wherein the magnetic resonance imaging apparatus is positioned intermediate the proximal end of the robotic arm and the subject during the surgical procedure, wherein the robotic arm is configured to extend from the proximal end of the robotic arm and through a bore in the magnetic resonance imaging apparatus to position the distal end of the robotic arm outside of the bore, proximate to the subject, and within the magnetic region of the magnetic resonance imaging apparatus.

9. The system of claim 8, wherein the distal end of the robotic arm is attached to an end effector configured for drug delivery.

10. The system of claim 8, wherein the distal end of the robotic arm is configured for inserting a needle into the subject for extracting a specimen.

11. The system of claim 8, wherein the robotic arm is configured for placing a stent into the subject.

12. The system of claim 8, wherein the robotic arm is attached to a needle configured for removing a sample from the subject.

13. The system of claim 8, wherein the robotic arm is attached to an ablation tool.

14. The system of claim 8, wherein the distal end of the robotic arm is attached to an end-effector containing a plurality of needles.

15. The system of claim 8, wherein the distal end of the robotic arm is attached to an end-effector configured for carrying one or more stents.

16. The system of claim 8, wherein the distal end of the robotic arm is attached to an end-effector configured for carrying one or more brachytherapy seeds.

17. The system of claim 8, wherein the robotic arm is configured for extracting a specimen for examination in a medical procedure from a list of medical procedures consisting of transperineal biopsy, transperineal LDR brachytherapy, transperineal HDR brachytherapy, transperineal laser ablation, transperineal cryoablation, transrectal HIFU, breast biopsies, deep brain stimulation (DBS), brain biopsy, liver biopsy, kidney biopsy, lung biopsy, coronary stent insertion, brain stent insertion, and intensity modulated radiation treatment guidance.

18. The system of claim 8, wherein the robotic arm comprises a motor, and wherein the imaging apparatus comprises an active noise cancellation module configured to:

detect noise generated by the motor; and remove detected noise from the acquired signals.

19. The system of claim 8, wherein the imaging apparatus is a single-sided magnetic resonance imaging apparatus.

* * * * *